(12) United States Patent
Wu et al.

(10) Patent No.: US 7,049,629 B2
(45) Date of Patent: May 23, 2006

(54) SEMICONDUCTOR POLYMERS AND DEVICES THEREOF

(75) Inventors: Yiliang Wu, Mississauga (CA); Ping Liu, Mississauga (CA); Lu Jiang, Albuquerque, NM (US); Beng S. Ong, Mississauga (CA)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 10/646,389

(22) Filed: Aug. 22, 2003

(65) Prior Publication Data
US 2005/0040394 A1   Feb. 24, 2005

(51) Int. Cl.
  *H01L 35/24*  (2006.01)
(52) U.S. Cl. ............................ 257/40; 438/99; 438/123
(58) Field of Classification Search ................. 438/99, 438/123; 257/40
See application file for complete search history.

(56) References Cited

U.S. PATENT DOCUMENTS 5,347,144 A * 9/1994 Garnier et al. ................. 257/40

(Continued)

OTHER PUBLICATIONS

Beng S. Ong et al., U.S. Appl. No. 10/392,639 on Fluorinated Polythiophenes And Devices Thereof, filed Mar. 19, 2003.

(Continued)

*Primary Examiner*—George Eckert
*Assistant Examiner*—Colleen E. Rodgers
(74) *Attorney, Agent, or Firm*—Eugene O. Palazzo; Fay, Sharpe, Fagan, Minnich & McKee, LLP

(57) ABSTRACT

An electronic device containing a thienylene-arylene polymer comprised of a repeating segment containing at least one 2,5-thienylene segment of (I) or (II), and at least one arylene segment of (IIIa), (IIIb), or (IIIc)

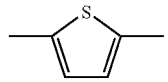

(I)

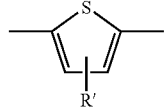

(II)

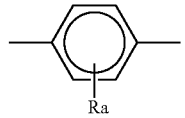

(IIIa)

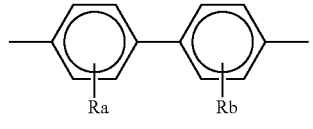

(IIIb)

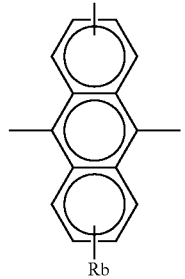

(IIIc)

Figure 1:
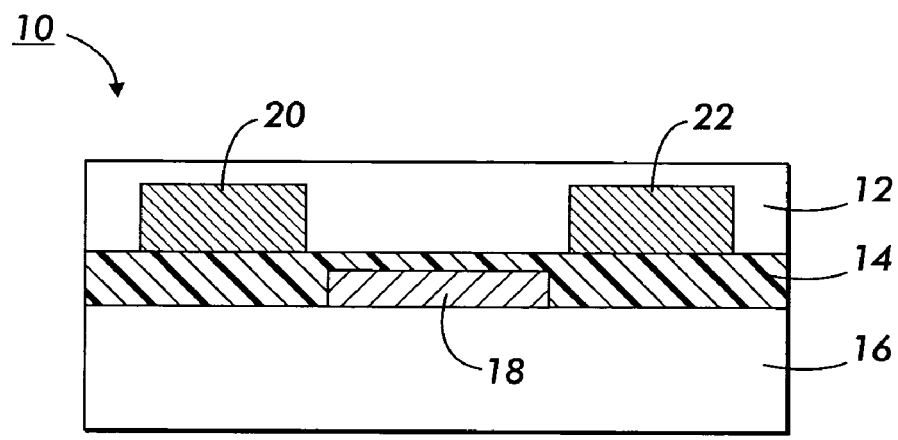

wherein each R is independently an alkyl or an alkoxy side chain; R' is halogen, alkyl, or alkoxy, and a and b represent the number of R segments or groups, and wherein the number of arylene segments (IIIa), (IIIb), and (IIIc) is from about 1 to about 3.

48 Claims, 2 Drawing Sheets

U.S. PATENT DOCUMENTS

| | | | |
|---|---|---|---|
| 5,619,357 A | 4/1997 | Angelopoulos et al. | 349/110 |
| 5,777,070 A | 7/1998 | Inbasekaran et al. | 528/394 |
| 5,969,376 A | 10/1999 | Bao | 257/40 |
| 6,107,117 A | 8/2000 | Bao et al. | 438/99 |
| 6,150,191 A | 11/2000 | Bao | 438/99 |
| 2003/0165713 A1* | 9/2003 | Oguma et al. | 428/690 |

OTHER PUBLICATIONS

Lu Jiang et al., U.S. Appl. No. 10/392,633 on Fluorinated Polythiophenes And Devices Thereof, filed Mar. 19, 2003.

Ping Liu et al., U.S. Appl. No. 10/392,592 on Polythiophenes and Devices Thereof, filed Mar. 19, 2003.

Beng S. Ong et al., U.S. Appl. No. 10/042,342 on Polythiophenes and Devices Thereof, filed Jan. 11, 2002.

Beng S. Ong et al., U.S. Appl. No. 10/042,356 on Polythiophenes and Devices Thereof, filed Jan. 11, 2002.

* cited by examiner

SEMICONDUCTOR POLYMERS AND DEVICES THEREOF

STATEMENT REGARDING FEDERALLY SPONSORED RESEARCH OR DEVELOPMENT

This invention was made with United States Government support under Cooperative Agreement No. 70NAN-BOH3033 awarded by the National Institute of Standards and Technology (NIST). The United States Government has certain rights in the invention.

COPENDING APPLICATIONS

In copending application U.S. Ser. No. (not yet assigned—D/A2543), filed concurrently herewith, the disclosure of which is totally incorporated herein by reference, there is illustrated a thienylene-arylene polymer comprised of a repeating segment containing at least one 2,5-thienylene unit selected from (I) and (II), and from about one to about three arylene units selected from (IIIa), (IIIb), and/or (IIIc)

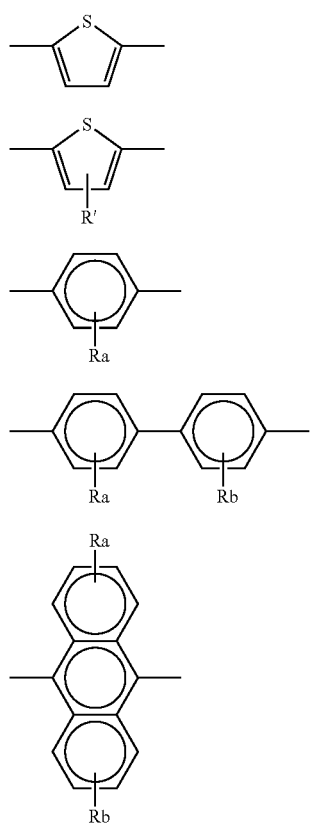

wherein R is an alkyl or an alkoxy; R' is halogen, alkyl, or alkoxy, and a and b represent the number of Rs.

In copending application U.S. Ser. No. 10/392,639, filed Mar. 19, 2003, titled Fluorinated Polythiophenes and Devices Thereof, the disclosure of which is totally incorporated herein by reference, there is illustrated an electronic device comprised of a polythiophene

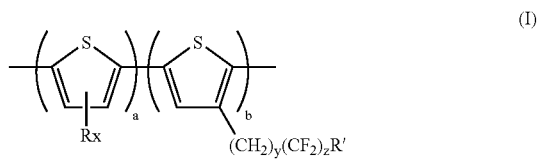

wherein R is an alkyl, alkoxy; x represents the number of R groups; R' is $CF_3$, alkoxy, alkyl, or optionally alkylene; y and z represent the number of segments; and a and b represent the mole fractions of each moiety, respectively, wherein the sum of a+b is equal to about 1.

In copending application U.S. Ser. No. 10/392,633, filed Mar. 19, 2003, titled Fluorinated Polythiophenes and Devices Thereof, the disclosure of which is totally incorporated herein by reference, there is illustrated a polythiophene comprising a repeating segment of the formula

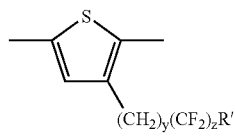

wherein R' is $CF_3$, alkyl or alkoxy; and y and z represent the number of repeating segments.

In copending application U.S. Ser. No. 10/392,592, filed Mar. 19, 2003, titled Polythiophenes and Devices Thereof, the disclosure of which is totally incorporated herein by reference, there is illustrated a device containing a polythiophene prepared by a metal halide polymerization in an aromatic solvent, and which polythiophene is comprised of at least one monomer unit selected from the group consisting of a 2,5-thienylene segment (I), and a 2,5-thienylene segment (II)

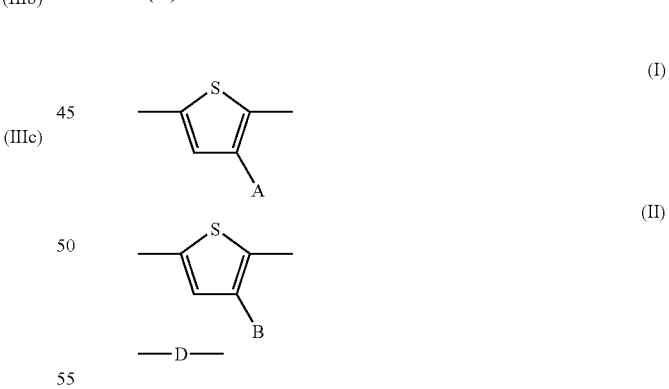

wherein A is alkyl, a halide, or alkoxy; B is a hydrogen atom, a halide, an alkyl or an alkoxy; and D is a divalent linkage for said (I) and (II).

Illustrated in copending application U.S. Ser. No. 10/042,342, filed on Jan. 11, 2002 and titled "Polythiophenes and Devices Thereof", the disclosure of which is totally incorporated herein by reference, is an electronic device containing a polythiophene derived from a monomer segment or monomer segments containing two 2,5-thienylene segments, (I) and (II), and an optional divalent linkage D

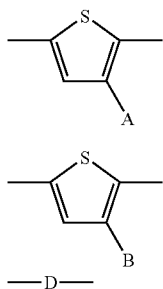

(I)

(II)

wherein A is a side chain; B is hydrogen or a side chain; and D is a divalent linkage, and wherein the number of A-substituted thienylene units (I) in the monomer segments is from about 1 to about 10, the number of B-substituted thienylene units (II) is from 0 to about 5, and the number of divalent linkages D is 0 or 1.

Illustrated in copending application U.S. Ser. No. 10/042,356, filed on Jan. 11, 2002 and titled "Polythiophenes and Devices Thereof", the disclosure of which is totally incorporated herein by reference, is an electronic device containing a polythiophene of Formula (I)

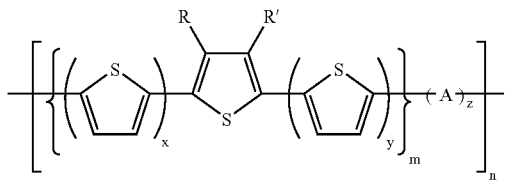

(I)

wherein R and R' are side chains; A is a divalent linkage; x and y represent the number of unsubstituted thienylene units or segments; z is 0 or 1, and wherein the sum of x and y is greater than zero; m represents the number of segments; and n represents the degree of polymerization.

Illustrated in copending application U.S. Ser. No. 10/042,360, the disclosure of which is totally incorporated herein by reference, filed on Jan. 11, 2002 and titled "Polythiophenes and Devices Thereof", a polythiophene

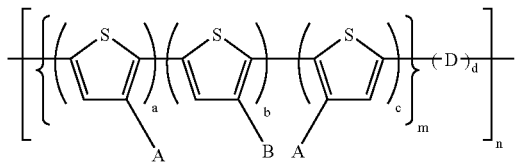

(III)

wherein A is a side chain; B is hydrogen or a side chain; D is a divalent linkage; a and c represent the number of A-substituted thienylenes; b is the number of B-substituted thienylene segments; d is 0 or 1; and n represents the degree of polymerization or the number of the monomer segments.

In U.S. Ser. No. 10/042,357, filed on Jan. 11, 2002 and titled "Polythiophenes and Devices Thereof", the disclosure of which is totally incorporated herein by reference, there are illustrated polythiophenes of the formula

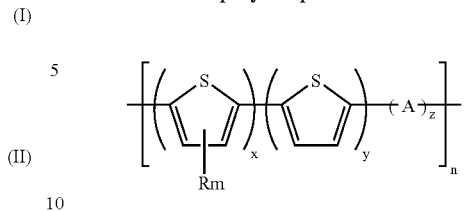

wherein R is a side chain; m is the number of substituents; A is a divalent linkage; x, y and z represent, respectively, the numbers of R substituted thienylene, unsubstituted thienylene, and divalent linkages A in the monomer segment with z being either 0 or 1; and n represents the number of the repeating monomer segments in the polymer chain or the degree of polymerization.

In copending application U.S. Ser. No. 10/042,359, filed on Jan. 11, 2002 and titled "Polythiophenes and Devices Thereof", the disclosure of which is totally incorporated herein by reference, there are illustrated polythiophenes of the formula

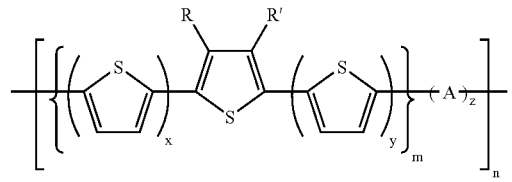

wherein R and R' are side chains; A is a divalent linkage; x and y represent the number of unsubstituted thienylene untis; z is 0 or 1, and wherein the sum of x and y is greater than zero; m represents the number of segments; and n represents the degree of polymerization In copending application U.S. Ser. No. 10/042,358, filed on Jan. 11, 2002 and titled "Polythiophenes and Electronic Devices Generated Therefrom", the disclosure of which is totally incorporated herein by reference, there is illustrated an electronic device containing a polythiophene

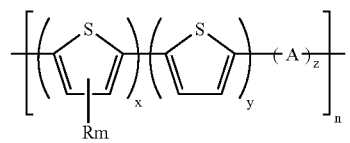

(I)

wherein R represents a side chain, m represents the number of R substituents; A is a divalent linkage; x, y and z represent, respectively, the number of $R_m$ substituted thienylenes, unsubstituted thienylenes, and divalent linkages A in the monomer segment subject to z being 0 or 1, and n represents the number of repeating monomer segments in the polymer or the degree of polymerization.

The appropriate components, processes thereof and uses thereof illustrated in the above copending applications may be selected for the present invention in embodiments thereof.

BACKGROUND

The present invention is generally directed to novel polymers like semiconductor polymers and electronic devices thereof. More specifically, the present invention in embodiments is directed to electronic devices containing a class of novel semiconductor polymers comprised of a repeating segment containing at least one arylene with a long side chain, preferably an alkyl or an alkoxy chain containing from about 5 to about 25 carbon atoms, and one to about 10 aromatic heterocyclic units. These polymers are capable of molecular self-organization under appropriate conditions, providing ordered microstructures in thin films which are suitable for microelectronic device applications, particularly thin film transistors (TFTs). In embodiments of the present invention there are illustrated semiconductor polymers which are comprised of one or more arylene units with long side chains and one or more substituted and/or unsubstituted 2,5-thienylene (also referred to as 2,5-thiophenediyl) segments or units, and aryl, and referred to as thienylene-arylene polymers. The aforementioned long side chains impart solubility characteristics to the polymer, and when properly positioned on the polymer backbone, assist in inducing and facilitating molecular organization of the polymer. In TFT devices, highly ordered microstructures in the semiconductor channel layers are of value to the efficient charge carrier transport between the source and drain electrodes, thus the TFT performance.

Semiconductor polymers, such as certain polythiophenes, have been reported for use in TFTs. A number of these polymers have some solubility in organic solvents and can thus be processed in solution for fabricating the semiconductor channel layers in TFTs. Solution processes, such as spin coating, solution casting, dip coating, screen printing, stamp printing, jet printing and the like, have been utilized to fabricate TFT channel layers with these materials. Fabrication via common solution processes could render the TFT manufacture simpler and more economical as compared to the costly conventional photolithographic processes typical of silicon-based devices such as hydrogenated amorphous silicon TFTs. Moreover, polymer semiconductor materials, such as polythiophenes, enable fabrication of TFTs on flexible substrates such as plastic substrates. TFTs on flexible substrates could enable the design of electronic devices with structural flexibility and mechanical durability characteristics. The use of plastic substrates together with organic or polymer transistor components can transform the traditionally rigid silicon TFT structure into a mechanically durable and structurally flexible polymer TFT design, which is of particular value to large area devices such as large area image sensors, electronic paper and other display media. Also, the selection of polymer TFTs for integrated circuit elements for low-end microelectronics, such as smart cards, radio frequency identification (RFID) tags, and memory/storage devices, may also greatly enhance their mechanical durability, and thus their useful life span. However, a number of the semiconductor polythiophenes are not stable when exposed to air as they become oxidatively doped by ambient oxygen, resulting in increased conductivity. The result is large off current, lower current on/off ratio, and positive turn-on voltage for the p-type devices fabricated from these materials. Accordingly, with a number of these materials, rigorous precautions have to be undertaken during materials processing and device fabrication to exclude environmental oxygen to avoid or minimize oxidative doping. These precautionary measures add to the cost of manufacturing therefore offsetting the appeal of polymer TFTs as an economical alternative to amorphous silicon technology, particularly for large area devices. These and other disadvantages are avoided or minimized in embodiments of the present invention.

REFERENCES

A number of organic semiconductor materials has been described for use in field-effect TFTs, which materials include organic small molecules such as pentacene, see for example D. J. Gundlach et al., "Pentacene organic thin film transistors—molecular ordering and mobility", *IEEE Electron Device Lett.*, Vol. 18, p. 87 (1997), to oligomers such as sexithiophenes or their variants, see for example F. Garnier et al., "Molecular engineering of organic semiconductors: Design of self-assembly properties in conjugated thiophene oligomers", *Amer. Chem. Soc.*, Vol. 115, p. 8716 (1993), and certain polythiophenes, such as poly(3-alkylthiophene), see for example Z. Bao et al., "Soluble and processable regioregular poly(3-hexylthiophene) for field-effect thin film transistor application with high mobility", *Appl. Phys. Lett.* Vol. 69, p. 4108 (1996). Although organic TFTs generally provide lower performance than their conventional silicon counterparts, such as silicon crystal or polysilicon TFTs, they are nonetheless sufficiently useful for applications in areas where high mobility is not required. These include large area devices, such as image sensors, active matrix liquid crystal displays and low-end microelectronics such as smart cards and RFID tags. TFTs fabricated from organic or polymer materials may be functionally and structurally more desirable than conventional silicon technology in the aforementioned areas in that they may offer mechanical durability, structural flexibility, and the potential of being able to be incorporated directly onto the active media of the devices, thus enhancing device compactness for transportability. However, a number of small molecule or oligomer-based devices rely on vacuum deposition techniques for fabrication. Vacuum deposition is selected primarily because the small molecular or oligomer materials are either insoluble or their solution processing by spin coating, solution casting, or stamp printing does not generally provide uniform thin films. On the other hand, polymer TFTs, such as those fabricated from regioregular polythiophenes of, for example, regioregular poly(3-alkylthiophene-2,5-diyl) by solution processes suffer from their propensity towards oxidative doping in air. Polymer TFTs fabricated from regioregular poly(3-alkylthiophene-2,5-diyl) in ambient conditions generally exhibit very large off-current, low current on/off ratios, and their performance characteristics degrade rapidly. For practical low cost TFT design, it is therefore of paramount importance to have a semiconductor material that is both air stable and solution processable, and where its performance is not adversely affected by ambient oxygen.

Other references that may be of interest include U.S. Pat. Nos. 6,150,191; 6,107,117; 5,969,376; 5,619,357, and 5,777,070.

FIGURES

Illustrated in FIGS. 1 to 4 are various representative embodiments wherein certain thienylene-arylene polymers are, for example, selected as the channel materials in thin film transistor configurations.

SUMMARY

It is a feature of the present invention to provide novel polymers like semiconductor polymers comprised of thienylene and arylene segments, and which polymers are useful for microelectronic device applications, particularly TFT devices.

It is another feature of the present invention to provide thienylene-arylene semiconductor polymers which are soluble in common organic coating solvents such as, for example, methylene chloride, tetrahydrofuran, toluene, xylene, mesitylene, chlorobenzene, dichlorobenzene, and the like, and thus can be fabricated by solution processes such as spin coating, screen printing, stamp printing, dip coating, solution casting, jet printing and the like.

Another feature of the present invention resides in providing electronic devices, such as TFTs, with a polymer channel layer, and which layer has a conductivity of from about $10^{-6}$ to about $10^{-9}$ S/cm (Siemens/centimeter) as measured by the known and conventional four probes method.

A further feature of the present invention is to provide thienylene-arylene semiconductor polymers which can be readily generated and which possess enhanced resistance to chemical doping by environmental oxygen.

Also, in yet another feature of the present invention there are provided thienylene-arylene semiconductor polymers and devices thereof, and which devices exhibit enhanced resistance to the adverse effects of oxygen, that is, these devices exhibit relatively high current on/off ratios, and their performance does not usually substantially degrade as rapidly as those fabricated from regioregular polythiophenes such as regioregular poly(3-alkylthiophene-3,5-diyl).

Additionally, in a further feature of the present invention there is provided a class of thienylene-arylene polymers with unique structural features which are conducive to molecular self-organization under appropriate processing conditions, and which structural features also enhance the stability of device performance. Proper molecular self-organization generally results in higher molecular structural order in thin films, which can be important to efficient charge carrier transport, and thus generating excellent, and in embodiments, high electrical performance characteristics.

Aspects of the present invention relate to polymers, especially polymers containing 2,5-thienylene segments of, for example, the formulas illustrated herein; a thin film transistor comprised of a substrate, a gate electrode, a gate dielectric layer, a source electrode, a drain electrode, and a semiconductor layer comprised of a polymer represented by Formula (IV-a) or (IV-b)

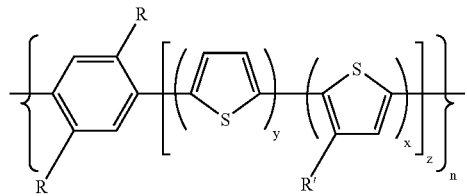

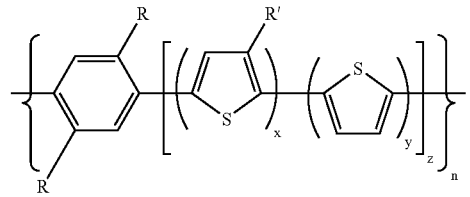

wherein R is a suitable substituent, such as an alkyl or alkoxy of from about 5 to about 25 carbon atoms; R' is halogen, alkyl or alkoxy, each with about 1 to about 30 carbon atoms; x and y represent the number of segments and are optionally from 0 to about 10, provided that the sum of x and y is at least equal to 1; z is about 1 to about 5, and n is the degree of polymerization, or the number of repeating segments in the polymer, and wherein n is optionally from about 5 to about 500; a thin film transistor comprised of a thienylene-arylene polymer comprised of a repeating segment containing at least one 2,5-thienylene segment of (I) or (II), and at least one arylene segment of (IIIa), (IIIb), or (IIIc)

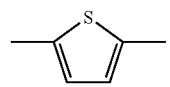

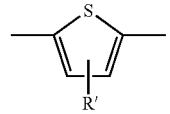

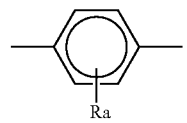

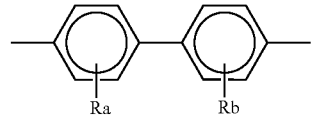

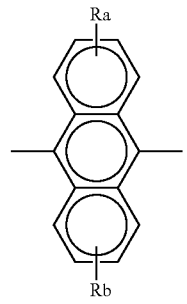

wherein each R is independently an alkyl or an alkoxy side chain; R' is halogen, alkyl, or alkoxy, and a and b represent the number of R segments or groups; electronic devices containing a thienylene-arylene polymer comprised of a repeating segment containing one or more 2,5-thienylene segments or units selected from (I) and (II), and an arylene segment selected from (IIIa), (IIIb), or (IIIc), or in embodiments, mixtures thereof

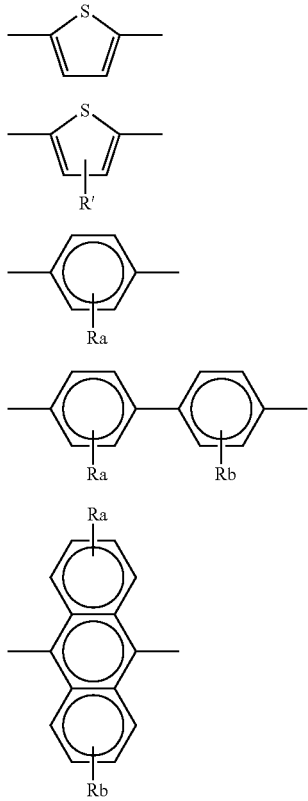

wherein R is, for example, alkyl or alkoxy, a and b are the number of R segments, and which R and R' can be halogen, alkyl or alkoxy; the number of 2,5-thienylene (I) and R'-substituted 2,5-thienylene units (II) in the repeating segment are preferably and independently selected from, for example, 0 to about 10, provided at least one of I and/or II is present in the repeating segment, and the number of arylene units selected for (IIIa), (IIIb), and (IIIc) is, for example, from about 1 to about 3 segments; an electronic device wherein R is an alkyl or an alkoxy side chain containing from about 5 to about 25 carbon atoms, and R' is alkyl or alkoxy of from about 1 to about 30 carbon atoms; an electronic device wherein R is alkyl or alkoxy containing from about 5 to about 10 carbon atoms, and R' is alkyl or alkoxy of from about 1 to about 15 carbon atoms; an electronic device wherein R is selected from the group consisting of pentyl, hexyl, heptyl, octyl, nonyl, decyl, undecyl, dodecyl, tridecyl, tetradecyl, pentadecyl, and the like, and R' is selected from the group consisting of methyl, ethyl, propyl, butyl, pentyl, hexyl, heptyl, octyl, nonyl, decyl, undecyl, dodecyl, tridecyl, tetradecyl, pentadecyl, isomers thereof, and the like; an electronic device wherein R and R' are independently selected from the group consisting of pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, pentadecyloxy, isomers thereof, and the like; a thin film transistor comprised of a substrate, a gate electrode, a gate dielectric layer, a source electrode and a drain electrode, and a semiconductor layer comprised of a thienylene-arylene polymer; a thin film transistor wherein R is alkyl or alkoxy containing from about 5 carbon atoms to about 25 carbon atoms, R' is alkyl or alkoxy containing from about 1 to about 30 carbon atoms, and wherein the source/drain electrodes and the gate dielectric layer are in contact with the semiconductive layer; a thin film transistor wherein R is pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, or pentadecyloxy, and R' is methyl, ethyl, propyl, butyl, pentyl, hexyl, heptyl, octyl, nonyl, decyl, undecyl, dodecyl, tridecyl, tetradecyl, pentyldecyl, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, or pentadecyloxy, and wherein the source/drain electrodes and the gate dielectric layer are in contact with the semiconductor polymer layer; a thin film transistor wherein the substrate is a plastic sheet of a polyester, a polyethylene, polypropylene, a polycarbonate, or a polyimide, the gate, source, and drain electrodes are each independently comprised of gold, nickel, aluminum, platinum, indium titanium oxide, a conductive polymer, a conductive ink or paste comprising a dispersion of conductive particles in a dispersing medium, and the gate dielectric layer is comprised of silicon nitride, silicon oxide, insulating polymers of a polyester, a polycarbonate, a polyacrylate, a poly(methacrylate), a poly(vinyl phenol), a polystyrene, a polyimide, an epoxy resin, an inorganic-organic composite material of nanosized metal oxide particles dispersed in a polymer, a polyimide, or an epoxy resin; and wherein the source/drain electrodes and the gate dielectric layer are in contact with the semiconductive layer; a thin film transistor wherein the substrate is glass or a plastic sheet; the gate, source and drain electrodes are each independently comprised of gold; the gate dielectric layer is comprised of an organic polymer of poly(methacrylate), polyacrylate, poly(vinyl phenol), polystyrene, polyimide, polycarbonate, or a polyester, and wherein the source/drain electrodes and the gate dielectric layer are in contact with the semiconductive polymer layer; a thin film transistor wherein the thienylene-arylene semiconductor polymer layer is formed by a solution process of spin coating, stamp printing, screen printing, or jet printing, and wherein the source/drain electrodes and the gate dielectric layer are in contact with the semiconductive layer; a thin film transistor wherein the gate, source and drain electrodes, dielectric, and semiconductor layers are formed from components deposited by solution processes of spin-coating, solution casting, stamp printing, screen printing, and jet printing, and wherein the source/drain electrodes and the gate dielectric layer are in contact with the semiconductive layer; a thin film transistor wherein the substrate is a plastic sheet of a polyester, a polyethylene, a polycarbonate, or a polyimide, and the gate, source and drain electrodes are comprised of conductive polymers of polystyrene sulfonate-doped poly(3,4-ethylenedioxythiophene), or a conductive ink or paste of a colloidal dispersion of a metal of silver or gold in a binder, and the gate dielectric layer is an organic polymer or an inorganic oxide particle-polymer composite, and wherein the source/drain electrodes and the gate dielectric layer are in contact with the semiconductive layer; a thin film transistor comprised of a substrate, a gate electrode, a gate dielectric layer, a source electrode and a drain electrode, and in contact with the source/drain electrodes and the gate dielectric layer, a semiconductor layer comprised of a thienylene-arylene polymer represented by Formulas (IV-a) and (IV-b)

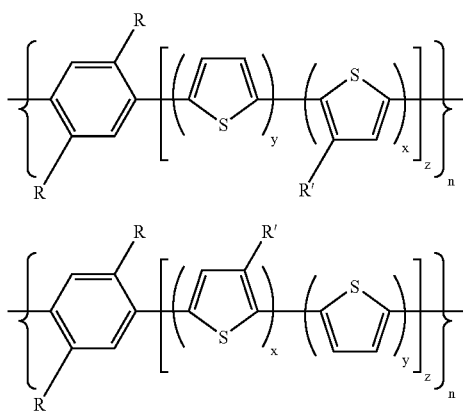

(IV-a)

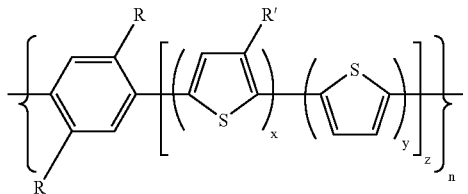

(IV-b)

wherein R is, for example, a suitable substituent, such as an alkyl or alkoxy chain of about 5 to about 30 carbon atoms; R' is a suitable substituent, such as halogen, alkyl or alkoxy, of about 1 to about 25 atoms, x and y are independently selected from the numbers 0, and about 1 to about 10, provided the sum of x and y is at equal to 1; z is about 1 to about 5, and n is the degree of polymerization, or the number of the repeating segments in the thienylene-arylene polymer, and is, for example, from about 5 to about 500; a thin film transistor wherein R is an alkyl or alkoxy side chain of from about 8 to about 14 carbon atoms, R' is alkyl or alkoxy of from about 1 to about 15 carbon atoms, x and y are independently 1 or 2, and z is 1; a thin film transistor wherein n of (IV-a) or (IV-b) is from about 5 to about 200; a thin film transistor wherein the number average molecular weight ($M_n$) of (IV-a) or (IV-b) is from about 2,000 to about 100,000, and wherein the weight average molecular weight ($M_w$) is from about 4,000 to about 500,000, each as measured by gel permeation chromatography using polystyrene standards; a thin film transistor wherein the number average molecular weight ($M_n$) Of (IV-a) or (IV-b) is from about 10,000 to about 30,000, and the weight average molecular weight ($M_w$) is from about 15,000 to about 100,000; a thin film transistor wherein R is phenyl, hexyl, heptyl, octyl, nonyl, decyl, undecyl, dodecyl, tridecyl, tetradecyl, or pentyldecyl; a thin film transistor wherein R is pentyloxy, hexyloxy, heptyloxy, octyloxy, nonyloxy, decyloxy, undecyloxy, dodecyloxy, tridecyloxy, or tetradecyloxy; a thin film transistor wherein R' is ethyl, propyl, butyl, pentyl, hexyl, heptyl, octyl, nonyl, decyl, undecyl, dodecyl, tridecyl, tetradecyl, or pentyldecyl; a thin film transistor wherein R' is methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, or pentadecyloxy; a thin film transistor wherein thienylene-arylene semiconductor polymer is selected from (1) through (20) wherein n represents the degree of polymerization, or the number of repeating segments of, for example, from about 5 to about 500

(1)

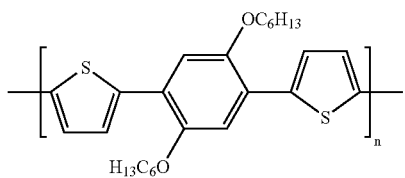

(2)

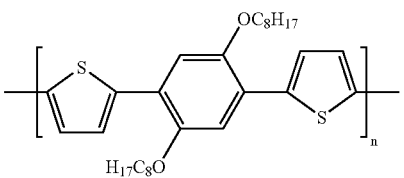

(3)

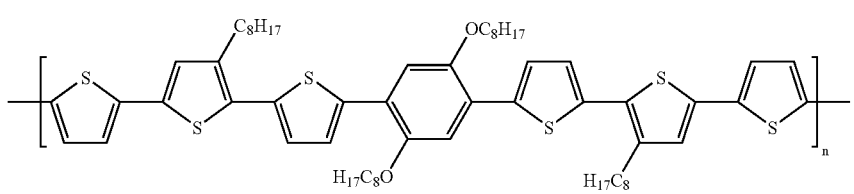

(4)

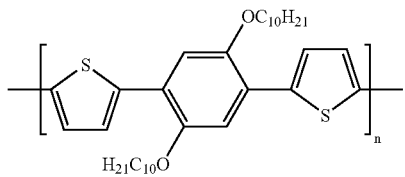

(5)

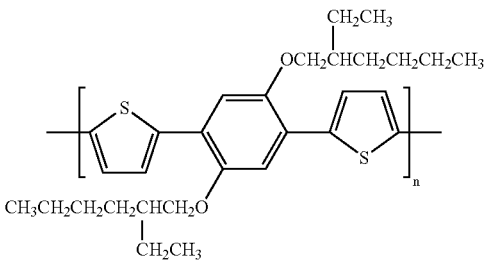

(6)

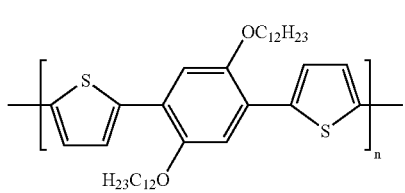

(7)

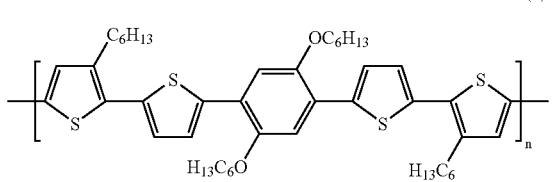

-continued
(8)
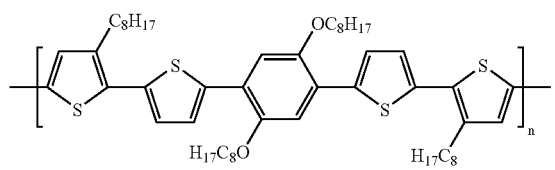
(9)
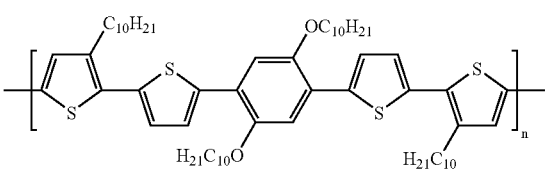
(10)
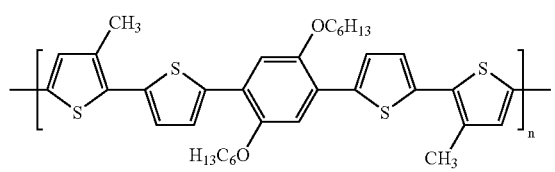
(11)
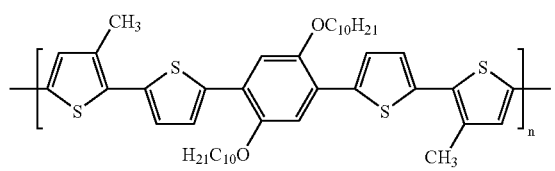
(12)
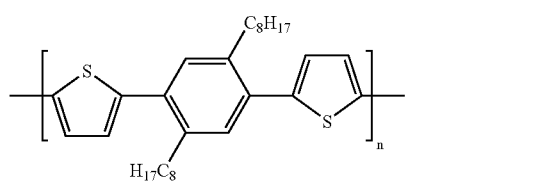
(13)
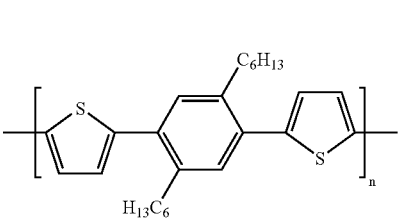
(14)
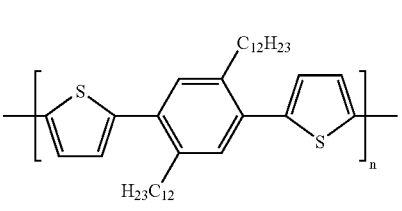
(15)
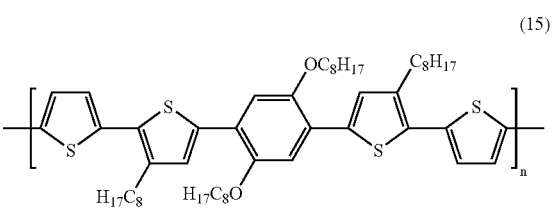
(16)
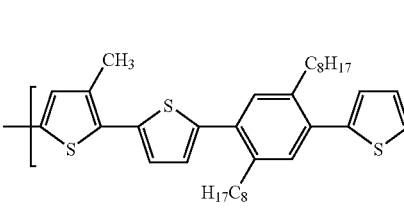
(17)
(18)
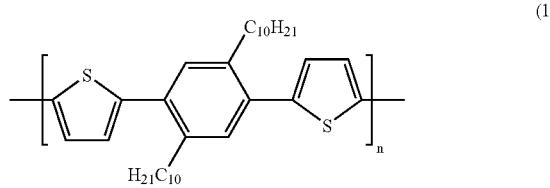
(19)
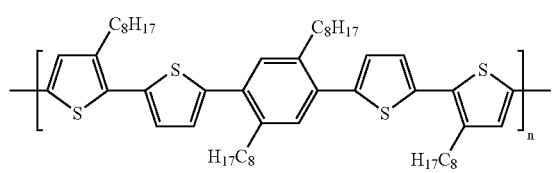
(20)
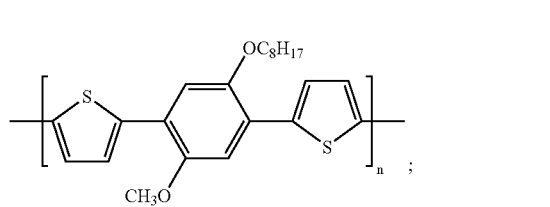
;

a thin film transistor wherein thienylene-arylene semiconductor polymer is selected from (1), (2), (7), (8), (9), (10), and (11), wherein n represents the degree of polymerization, or the number of repeating segments of from about 5 to about 500

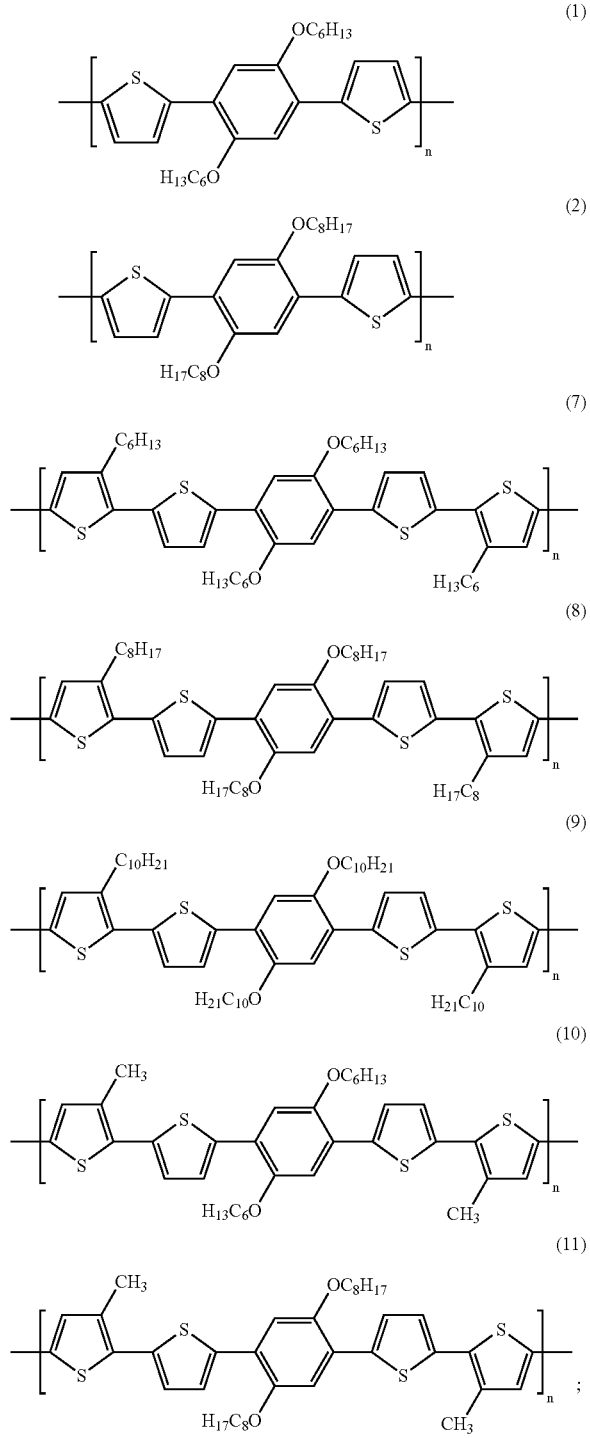

a thin film transistor wherein the thienylene-arylene semiconductor polymer is selected from (2), (8), (9), (10), and (11), wherein n represents the degree of polymerization, or the number of repeating segments, of from about 5 to about 500, or from about 10 to about 200

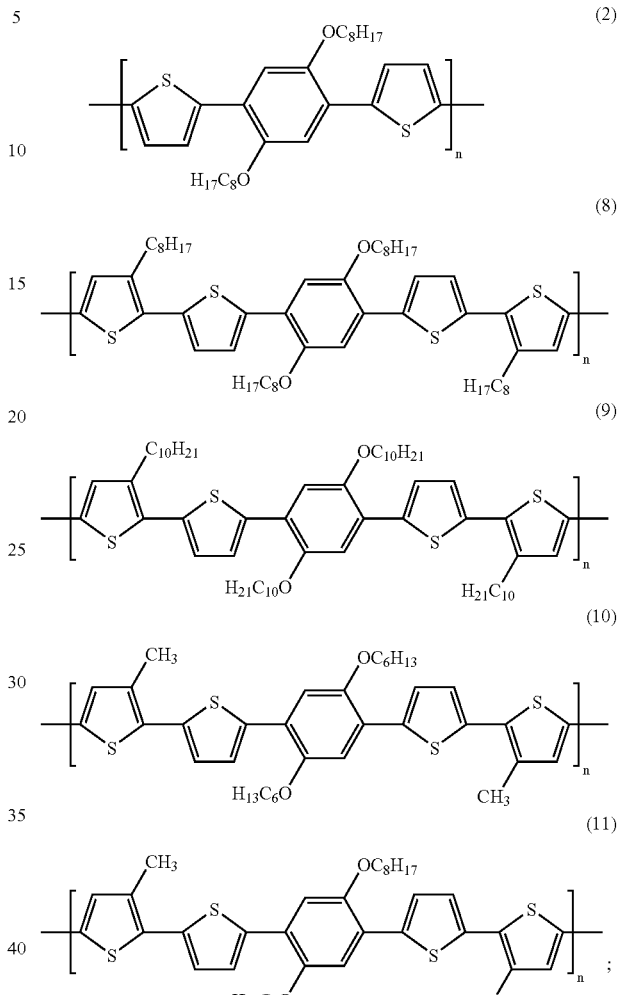

a thin film transistor wherein the substrate is a plastic sheet of a polyester, a polycarbonate, or a polyimide; the gate, source, and drain electrodes are each independently comprised of gold, nickel, aluminum, platinum, or indium titanium oxide, and the like in combination with a gate dielectric layer comprised of silicon nitride, silicon oxide, insulating polymers of polyester, polycarbonates, polyacrylate, poly(methacrylate), poly(vinyl phenol), polystyrene, polyimide, or an epoxy resin; a thin film transistor device wherein the substrate is glass or a plastic sheet; the gate, source and drain electrodes are each independently comprised of gold in combination with a gate dielectric layer comprised of an organic polymer of a polyester, a polycarbonate, a polyacrylate, a poly(methacrylate), a poly(vinyl phenol), a polystyrene, a polyimide, an epoxy resin, or an inorganic-organic composite of nanosized metal oxide particles dispersed in a polymer of a polyester, a polyimide, or an epoxy resin; a thin film transistor device wherein the thickness of the substrate is from about 10 micrometers to about 10 millimeters; the thickness of the gate dielectric layer is from about 10 nanometers to about 1 micrometer, the thickness of the thienylene-arylene semiconductor polymer layer is from about 10 nanometers to about 1 micrometer, the thickness of the gate electrode layer is from about 10 nanometers to about 10 micrometers, and the thickness of the source or drain electrode is from about 40 nanometers to about 1 micrometer, a thin film transistor device wherein the thienylene-arylene semiconductor polymer layer is formed by a solution process of spin coating, stamp or screen printing, or jet printing; a thin film transistor wherein the electrodes (gate, source and drain), gate dielectric, and semiconductor layers are formed from materials which can be deposited by solution processes such as spin-coating, solution casting, stamp printing, screen printing, and jet printing; a thin film transistor wherein the substrate is a polyester, a polycarbonate, or a polyimide, and the gate, source and drain electrodes are comprised of a conductive polymers such as polystyrene sulfonate-doped poly(3,4-ethylenedioxythiophene) or conductive ink or paste of a colloidal dispersion of silver or gold in a polymer binder, and the gate dielectric layer is organic polymer or inorganic oxide particle-polymer composite; a thin film transistor wherein the thickness of the substrate is from about 5 micrometers to about 7 millimeters, with a preferred thickness being from about 50 to about 100 micrometers for a flexible plastic substrate and of 1 to about 10 millimeters for a rigid substrate such as glass or silicon; the thickness of the gate dielectric layer is from about 10 nanometers to about 1 micrometer with a preferred thickness being from about 100 nanometers to about 500 nanometers, and the thickness of the thienylene-arylene semiconductor polymer layer is from about 10 nanometers to about 1 micrometer with the preferred thickness being from about 25 to about 100 nanometers; the thickness of the gate electrode layer is about 10 nanometers to about 7 micrometers with a preferred thickness of about 10 to about 200 nanometers for metal films, and about 1 to about 10 micrometers for polymer conductors; the thickness of the source or drain electrode is about 35 nanometers to 1 micrometer with a preferred thickness of about 100 to about 400 nanometers; and wherein the thienylene-arylene semiconductor polymer is comprised of a repeating segment containing one or more 2,5-thienylene units selected from (I) and (II), and an alkyl or alkoxy substituted arylene selected from (IIIa), (IIIb), and (IIIc):

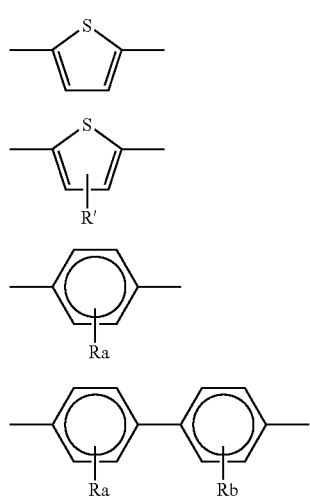

-continued

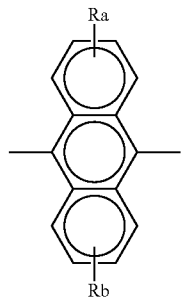

(IIIc)

wherein R is alkyl or alkoxy side chain with a and b being the number of Rs, such as 1 or 2, and R' is a halogen atom, alkyl or alkoxy; the number of 2,5-thienylene (I) and R'-substituted 2,5-thienylene units (II) in the repeating segment are, more specifically, from 0 to about 10, provided at least one of them is present in the monomer, and the number of arylene units (IIIa), (IIIb) or (IIIc) is about 1 to about 2.

The thienylene-arylene semiconductor polymers of the present invention in embodiments can be illustrated by Formulas (IV-a) and (IV-b)

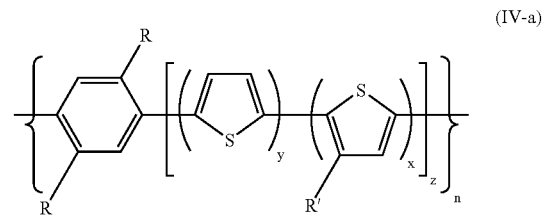

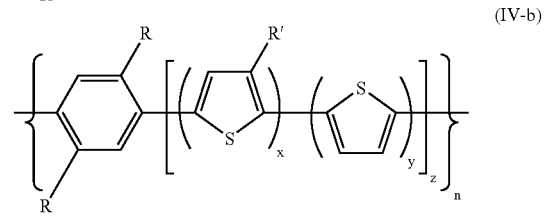

wherein R is a suitable substituent, such as alkyl or alkoxy side chain containing, for example, about 5 to about 25 carbon atoms; R' is a suitable substituent, such as halogen, alkyl or alkoxy, of about 1 to about 25 carbon atoms; x and y represent the number of segments, which number is, for example, from 0 to about 10, providing that the sum of x and y is equal to 1; z is a number of from about 1 to about 5, and n is the degree of polymerization or the number of the monomer units in thienylene-arylene polymer (IV), and can be, for example, from about 10 to over 400, and more specifically, from about 20 to about 200. The number average molecular weight ($M_n$) of thienylene-arylene semiconductor polymer (IV) can be, for example, from about 2,000 to about 100,000, and more specifically, from about 4,000 to about 50,000, and their weight average molecular weight ($M_w$) can be from about 4,000 to about 500,000, and more specifically, from about 5,000 to about 100,000, both as measured by gel permeation chromatography using polystyrene standards. Examples of R and R' include alkyl containing, for example, from about 5 to about 25 carbon atoms, such as pentyl, hexyl, heptyl, octyl, nonyl, decyl, undecyl, dodecyl, tridecyl, tetradecyl, pentyldecyl, and the like, alkoxy, such as for example pentyloxy, hexyloxy, heptyloxy, octyloxy, nonyloxy, decyloxy, undecyloxy, dodecyloxy, tridecyloxy, tetradecyloxy, pentadecyloxy and the like, a polyether chain, such as polyethylene oxide, perhaloalkyl, such as perfluoroalkyl, and the like; examples of R' include halogen such as bromine atom, methyl, methoxy, ethyl, ethoxy, propyl propoxy, butyl, butoxy, pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentyldecyl, pentadecyloxy, and the like.

Specific illustrative thienylene-arylene semiconductor polymers in embodiments include the following, and wherein n represents the degree of polymerization or the number of repeating segments

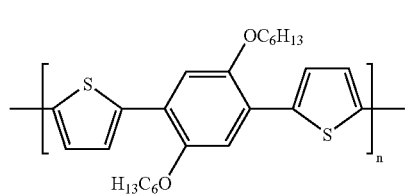
(1)

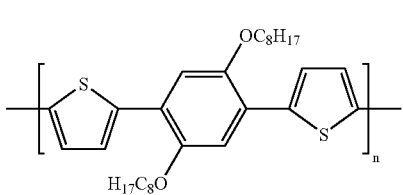
(2)

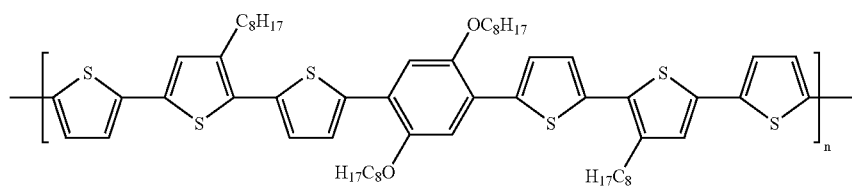
(3)

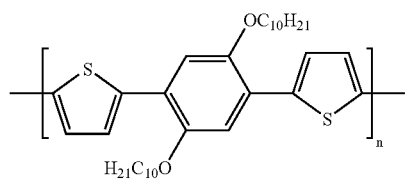
(4)

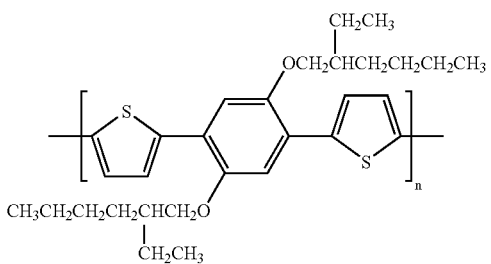
(5)

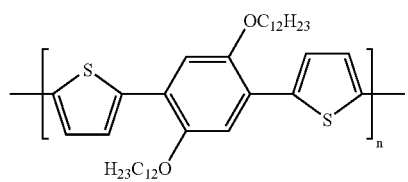
(6)

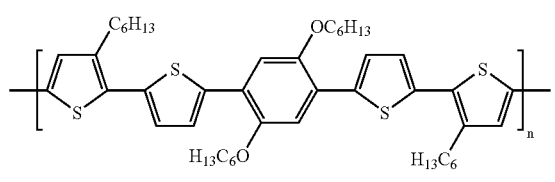
(7)

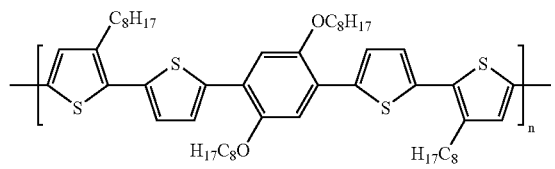
(8)

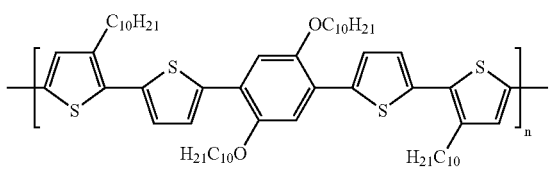
(9)

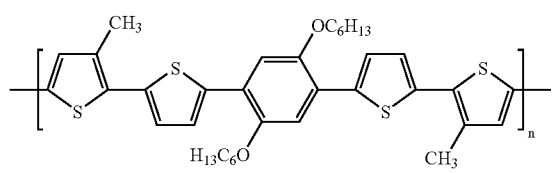
(10)

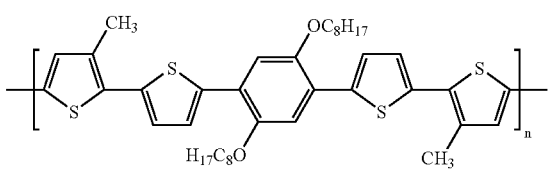
(11)

-continued

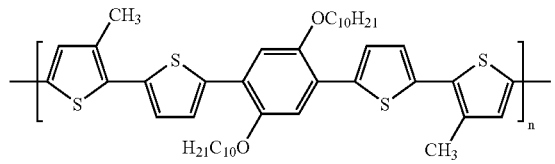
(12)

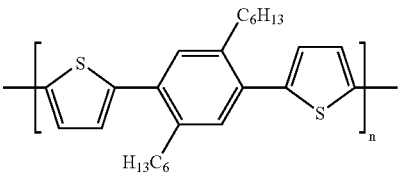
(13)

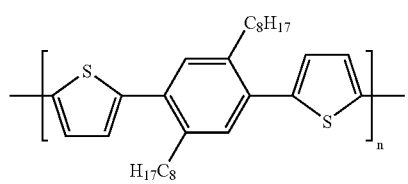
(14)

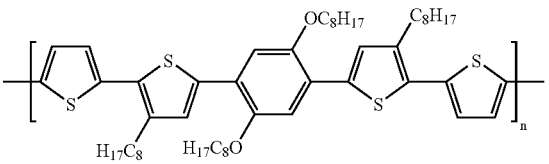
(15)

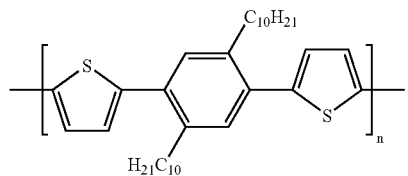
(16)

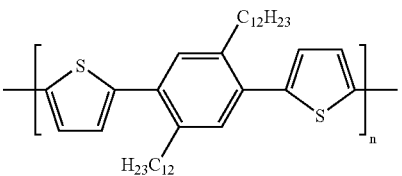
(17)

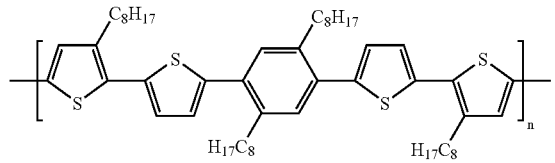
(18)

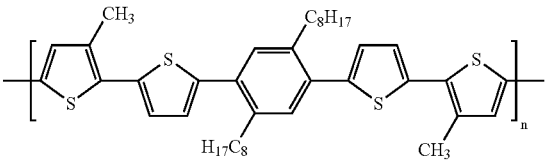
(19)

(20)

and wherein n represents the number of repeating segments and is, for example, a number of from about 25 to about 200, or from about 5 to about 200.

The thienylene-arylene semiconductor polymers of the present invention in embodiments are soluble in common organic coating solvents, for example they possess a solubility of at least about 0.1 percent by weight, and more specifically, from about 0.5 percent to about 5 percent by weight in such solvents as methylene chloride, 1,2-dichloroethane, tetrahydrofuran, toluene, xylene, mesitylene, chlorobenzene, and the like. Moreover, the thienylene-arylene polymers of the present invention in embodiments when fabricated as semiconductor channel layers in thin film transistor devices provide a stable conductivity of, for example, from about $10^{-9}$ S/cm to about $10^{-6}$ S/cm, and more specifically, from about $10^{-8}$ S/cm to about $10^{-7}$ S/cm as determined by conventional four-probe conductivity measurements.

A number of synthetic procedures are suitable for the preparation of the thienylene-arylene semiconductor polymers of the present invention, depending primarily on the specific thienylene-arylene polymers desired. As an illustration, polymer (VI-a), a member of the thienylene-arylene semiconductor polymers (IV-a) and (IV-b) with x=0, y=1, and R=an alkoxy chain, and polymer (VI-b), another member of (IV-a) and (IV-b) with x=1, y=1, R'=alkyl, and R=an alkoxy chain, can be prepared from the corresponding monomers (V-a) and (V-c), respectively, via the metal halide-mediated oxidative coupling polymerization according to Scheme 1. Polymer (VI-a) can also be readily prepared from the intermediate (V-b) by treating with or in the presence of a Reike zinc/Ni(dppe)Cl$_2$.

Scheme 1

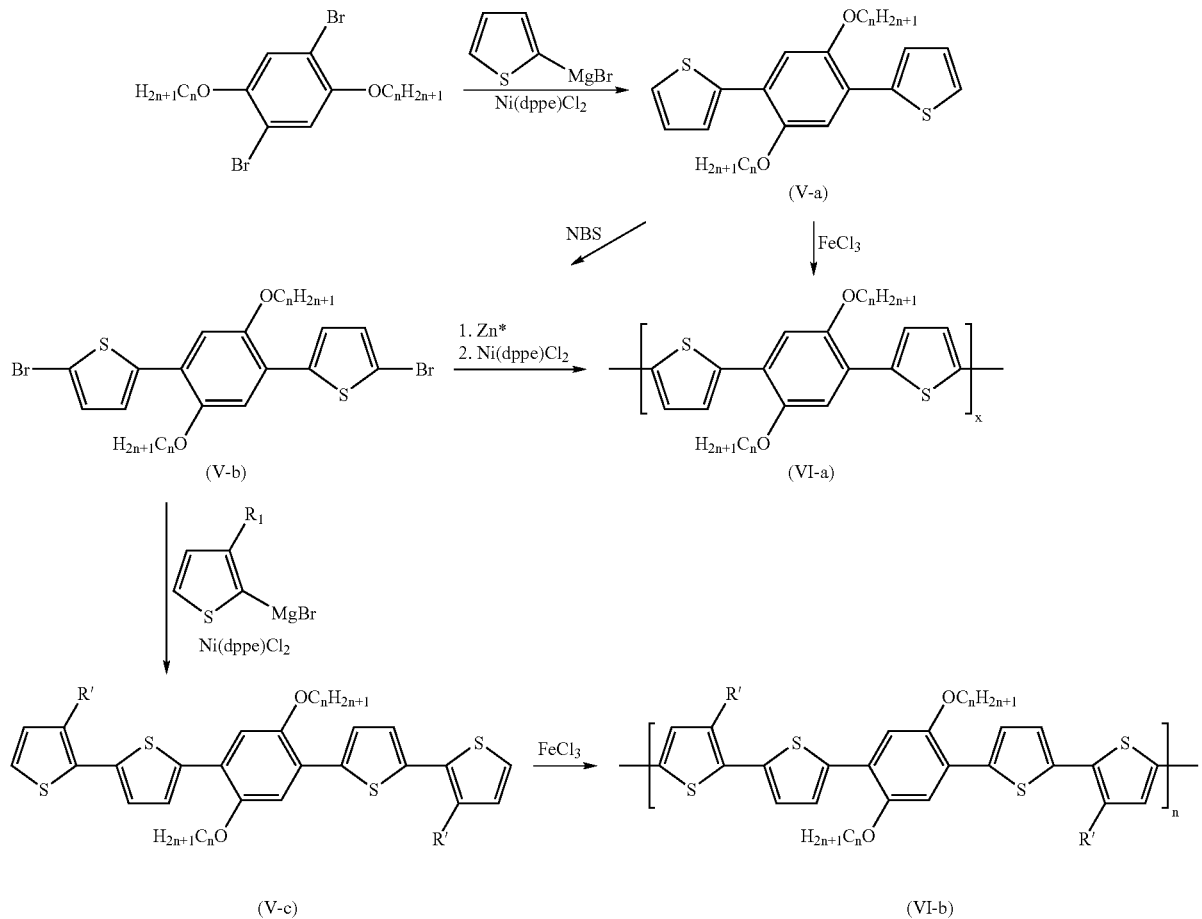

Both the monomers (V-a) and (V-c) contain side chains which are strategically placed on the phenylene and thienylene segments which upon polymerization, there results a thienylene-arylene polymer with side chains which are regioregularly positioned on the polymer backbones. Unlike the preparation of regioregular polythiophenes, such as poly(3-alkylthiophene-2,5-diyl) which require regioregular coupling reaction, the thienylene-arylene polymers of the present invention can be prepared by general polymerization techniques without regioregularity complications. Specifically, $FeCl_3$-mediated oxidative coupling has been utilized in the preparation of thienylene-arylene polymers (VI-a) and (VI-b).

The polymerization is generally conducted by adding a solution of 1 molar equivalent of monomer (V-a) or monomer (V-c) in a chlorinated solvent, such as chloroform, to a suspension of about 1 to about 5 molar equivalents of anhydrous $FeCl_3$ in chloroform. The resultant mixture is permitted to react at a temperature of about 25° C. to about 60° C. under a blanket of dried air or inert gas, or with a slow stream of dried air or inert gas bubbling through the reaction mixture for a period of, for example, about 30 minutes to about 72 hours. After the reaction, the thienylene-arylene polymer product is isolated by washing the reaction mixture with water or a dilute aqueous hydrochloric acid solution, stirring with a dilute aqueous ammonium solution for a period of about 15 minutes to about 60 minutes, followed by washing with water, precipitation from a nonsolvent, and optionally extracting the thienylene-arylene polymer product via soxhlet extraction with appropriate solvents such as methanol, toluene, xylene, chlorobenzene, and the like. The thienylene-arylene polymer product obtained can be further purified by precipitation from a suitable solvent such as methanol or acetone. For the Reike zinc method, 10 mmolar equivalents of (V-b) in anhydrous tetrahydrofuran are added dropwise over a period of about 20 minutes to about 40 minutes to a well stirred suspension of 11 mmolar equivalent of freshly prepared Reike Zn in anhydrous tetrahydrofuran, and the resulting mixture is then permitted to react for about 30 minutes to about 2 hours at room temperature, about 22° C. to about 25° C. Subsequently, a suspension of about 0.1 mmolar equivalent of $Ni(dppe)Cl_2$ in anhydrous tetrahydrofuran is slowly added over a period of about 10 minutes to about 20 minutes, and the mixture is then heated at about 40° C. to about 65° C. for about 2 to about 5 hours. The reaction mixture is then poured into dilute hydrochloric acid solution in methanol with vigorous stirring to precipitate the polymer product, which product is redissolved in hot tetrahydrofuran and then reprecipitated from dilute ammonia solution in methanol.

FIGURES

In FIG. 1 there is schematically illustrated a TFT configuration 10 comprised of a substrate 16, in contact therewith a metal contact 18 (gate electrode) and a layer of an insulating dielectric layer 14 on top of which two metal contacts, 20 and 22 (source and drain electrodes), are deposited. Over and between the metal contacts 20 and 22 is the thienylene-arylene semiconductor layer 12 as illustrated herein.

Figure 2:
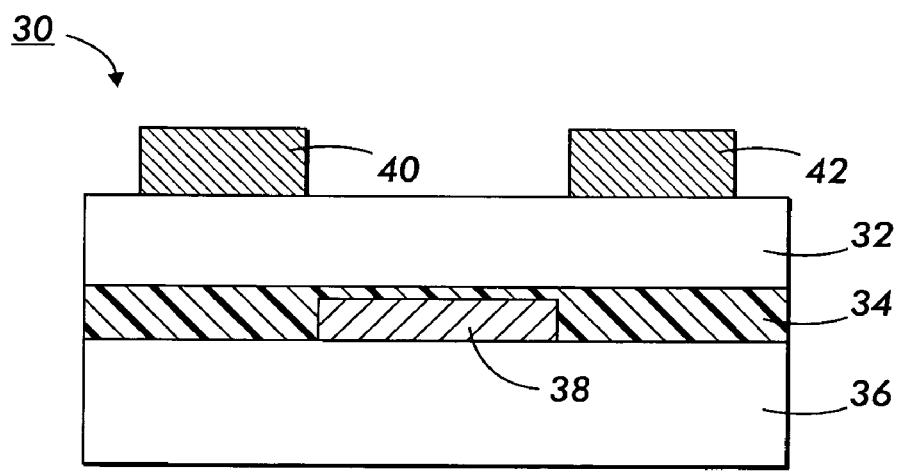

FIG. 2 schematically illustrates a TFT configuration 30 comprised of a substrate 36, a gate electrode 38, a source electrode 40 and a drain electrode 42, an insulating dielectric layer 34, and the thienylene-arylene semiconductor layer 32.

Figure 3:
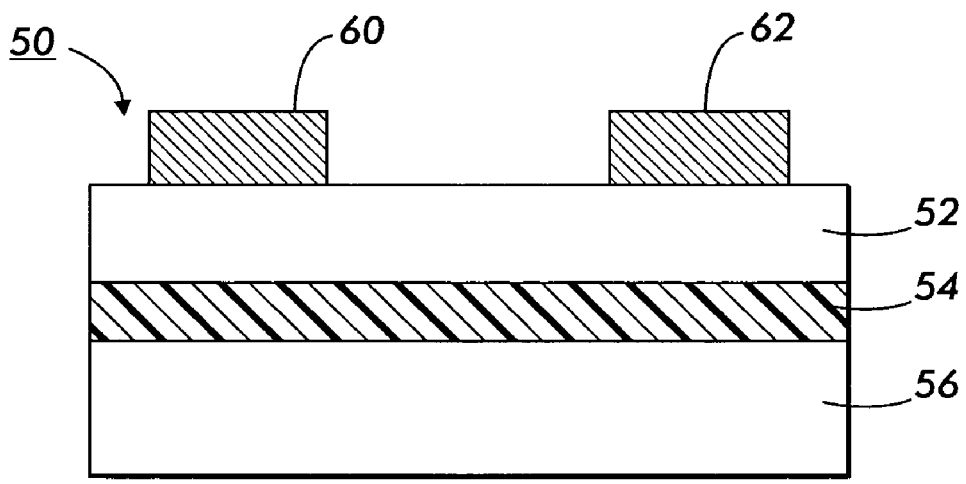

FIGS. 3 schematically illustrates another TFT configuration 50 comprised of a heavily n-doped silicon wafer 56 which acts as a gate electrode, a thermally grown silicon oxide dielectric layer 54, and the thienylene-arylene semiconductor layer 52, on top of which are deposited a source electrode 60 and a drain electrode 62.

Figure 4:
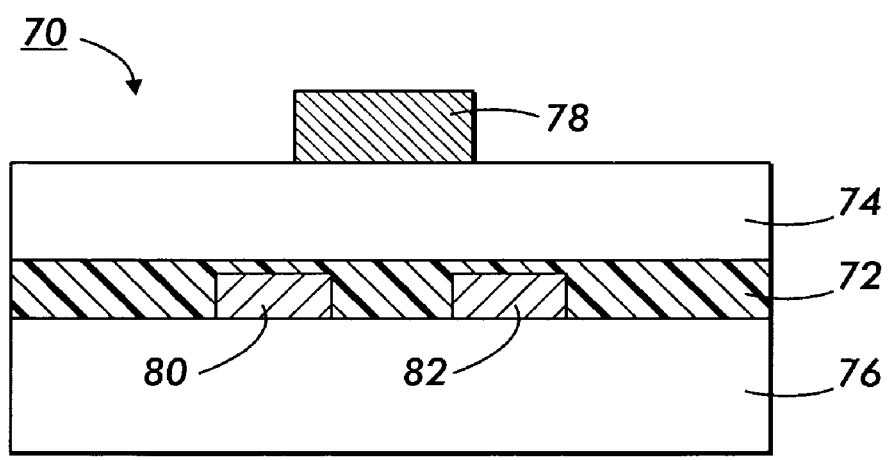

FIG. 4 schematically illustrates an additional TFT configuration 70 comprised of substrate 76, a gate electrode 78, a source electrode 80, a drain electrode 82, the thienylene-arylene semiconductor layer 72, and an insulating dielectric layer 74.

In some embodiments of the present invention, an optional protecting layer, such as a polymer, may be incorporated on top of each of the transistor configurations of FIGS. 1, 2, 3 and 4. For the TFT configuration of FIG. 4, the insulating dielectric layer 74 may also function as a protecting layer.

In embodiments and with further reference to the present invention and the Figures, the substrate layer may generally be a silicon material inclusive of various appropriate forms of silicon, a glass plate, a plastic film or a sheet, and the like depending on the intended applications. For structurally flexible devices, a plastic substrate, such as for example polyester, polycarbonate, polyimide sheets, and the like, may be selected. The thickness of the substrate may be, for example, from about 10 micrometers to over 10 millimeters with a specific thickness being from about 50 to about 100 micrometers, especially for a flexible plastic substrate and from about 1 to about 10 millimeters for a rigid substrate such as glass or silicon.

The insulating dielectric layer, which can separate the gate electrode from the source and drain electrodes, and can be in contact with the semiconductor layer, can generally be an inorganic material film, an organic polymer film, or an organic-inorganic composite film. The thickness of the dielectric layer is, for example, from about 10 nanometers to about 1 micrometer with a more specific thickness being about 100 nanometers to about 500 nanometers. Illustrative examples of inorganic materials suitable as the dielectric layer include silicon oxide, silicon nitride, aluminum oxide, barium titanate, barium zirconate titanate, and the like; illustrative examples of organic polymers for the dielectric layer include polyesters, polycarbonates, poly(vinyl phenol), polyimides, polystyrene, poly(methacrylate)s, poly(acrylate)s, epoxy resin, and the like; and illustrative examples of inorganic-organic composite materials include nanosized metal oxide particles dispersed in polymers such as polyester, polyimide, epoxy resin, and the like. The insulating dielectric layer is generally of a thickness as illustrated herein, such as from about 50 nanometers to about 500 nanometers, depending on the dielectric constant of the dielectric material used. More specifically, the dielectric material has a dielectric constant of, for example, at least about 3, thus a suitable dielectric thickness of about 300 nanometers can provide a desirable capacitance, for example, of about $10^{-9}$ to about $10^{-7}$ F/cm$^2$.

Situated, for example, between and in contact with the dielectric layer and the source/drain electrodes is the active semiconductor layer comprised of the thienylene-arylene semiconductor polymers illustrated herein, and wherein the thickness of this layer is generally, for example, about 10 nanometers to about 1 micrometer, or about 40 to about 100 nanometers, and the like. This layer can generally be fabricated by solution processes, such as spin coating, casting, screen, stamp, or jet printing of a solution of the thienylene-arylene semiconductor polymers of the present invention.

The gate electrode can be a thin metal film, a conducting polymer film, a conducting film generated from a conducting ink or paste, or the substrate itself (for example, heavily doped silicon). Examples of gate electrode materials include but are not limited to aluminum, gold, chromium, indium tin oxide, conducting polymers, such as polystyrene sulfonate-doped poly(3,4-ethylenedioxythiophene) (PSS/PEDOT), a conducting ink/paste comprised of carbon black/graphite or colloidal silver dispersion contained in a polymer binder, such as ELECTRODAG® available from Acheson Colloids Company and silver filled electrically conductive thermoplastic ink available from Noelle Industries, or the like. The gate layer can be prepared by vacuum evaporation, sputtering of metals or conductive metal oxides, coating from conducting polymer solutions or conducting inks or dispersions by spin coating, casting or printing. The thickness of the gate electrode layer is, for example, from about 10 nanometers to about 10 micrometers, and more specifically, from about 10 to about 200 nanometers for metal films and about 1 to about 10 micrometers for polymer conductors.

The source and drain electrode layer can be fabricated from materials which, for example, provide a low resistance ohmic contact to the semiconductor layer. Typical materials suitable for use as source and drain electrodes include the gate electrode materials such as gold, nickel, aluminum, platinum, conducting polymers, and conducting inks. Typical thickness of this layer is about, for example, from about 40 nanometers to about 1 micrometer with the more specific thickness being about 100 to about 400 nanometers. The TFT devices contain a semiconductor channel with a width W and length L. The semiconductor channel width may be, for example, from about 10 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers. The source electrode is grounded and a bias voltage of generally about +20 volts to about 80 volts is applied to the drain electrode to collect the charge carriers transported across the semiconductor channel when a voltage of generally about +20 volts to about −80 volts is applied to the gate electrode.

Other known materials not recited herein for the various components of the TFT devices of the present invention can also be selected in embodiments.

The following Examples are provided.

General Procedure a) Device Fabrication (Test Device):

There was selected a top-contact thin film transistor configuration as schematically described by FIG. 3 as the primary device structure.

The device was comprised of an n-doped silicon wafer with a thermally grown silicon oxide layer of a thickness of about 110 nanometers thereon. The wafer functioned as the gate electrode while the silicon oxide layer acted as the gate dielectric and had a capacitance of about 32 nF/cm$^2$ (nanofarads/square centimeter). The fabrication of the device was accomplished at ambient conditions without any precautions to exclude the materials and device from exposure to ambient oxygen, moisture, or light. The silicon wafer was first cleaned with methanol, air dried, and then immersed in a solution of octyltrichlorosilane in toluene for 10 minutes at 60° C. Subsequently, the wafer was washed with toluene, isopropanol and dried. The semiconductor layer of about 30 nanometers to about 100 nanometers in thickness was then deposited on top of the silicon oxide dielectric layer by spin coating at a speed of 1,000 rpm for about 35 seconds, and dried in vacuo at 80° C. for 20 hours. The solution used in fabricating the semiconductor layer was comprised of 1 percent by weight of the semiconducting polymer in an appropriate solvent, and was filtered through a 0.2 μm filter before use. Thereafter, the gold source and drain electrodes were deposited on top of the semiconductor layer by vacuum deposition through a shadow mask with various channel lengths and widths, thus providing a series of transistors of various dimensions. The devices after fabrication were retained in a dry atmosphere of about 30 percent relative humidity in the dark before and after evaluation.

b) TFT Device Characterization:

The evaluation of field-effect transistor performance was accomplished in a black box at ambient conditions using a Keithley 4200 SCS semiconductor characterization system. The carrier mobility, μ, was calculated from the data in the saturated regime (gate voltage, $V_G$<source-drain voltage, $V_{SD}$) according to equation (1)

$$I_{SD}=C_i\mu(W/2L)(V_G-V_T)^2 \quad (1)$$

where $I_{SD}$ is the drain current at the saturated regime, W and L are, respectively, the semiconductor channel width and length, Ci is the capacitance per unit area of the gate dielectric layer, and $V_G$ and $V_T$ are, respectively, the gate voltage and threshold voltage. $V_T$ of the device was determined from the relationship between the square root of $I_{SD}$ at the saturated regime and $V_G$ of the device by extrapolating the measured data to $I_{SD}$=0.

Another valuable property associated with field-effect transistors is its current on/off ratio, that is the ratio of the saturation source-drain current when the gate voltage $V_G$ is equal to or greater than the drain voltage $V_D$ to the source-drain current when the gate voltage $V_G$ is zero.

COMPARATIVE EXAMPLE

A series of comparative thin film transistors were fabricated using the known regioregular polythiophene, poly(3-hexythiophene-2,5-diyl), which is commonly known as P3HT. This material was purchased from Aldrich Chemical and was purified by three successive precipitations of its solution in chlorobenzene from methanol.

The devices were fabricated in ambient conditions in accordance with the procedure as described hereinbefore. Using transistors with a dimension of W (width)=5,000 μm and L (length)=60 μm, the following average properties from at least five transistors were obtained:

Mobility: ~1.2×10$^{-2}$ cm$^2$/V.sec
Initial on-off ratio: ~2×10$^3$
On-off ratio after 5 days: 5 to 10

The observed low initial current on/off ratios are an indication of the propensity of poly(3-hexythiophene-2,5-diyl) to undesirable oxidative doping, that is the instability of poly(3-hexythiophene-2,5-diyl) in the presence of ambient oxygen. The reductions in the current on/off ratios over just a five day period further confirm the functional instability of poly(3-hexythiophene-2,5-diyl) at ambient conditions.

Eample I

Preparation of Thienylene-arylene (2)

a) 1,4-bis(2-thienyl)-2,5-dioctyloxybenzene (V-a)

A solution of 1,4-dibromo-2,5-dioctyloxybezene (6.580 grams, 13.365 mmol) in 15 milliliters of anhydrous tetrahydrofuran (THF) was added slowly over a period of 20 minutes to a mechanically stirred suspension of magnesium turnings (0.975 gram, 40.095 mmol) in 5 milliliters of THF in a 250 milliliter round-bottomed flask under an inert argon atmosphere. The resultant mixture was stirred at 60° C. for 3.5 hours. Subsequently, the resulting mixture was added to a mixture of 2-bromothiophene (5.447 grams, 33.412 mmol) and [1,3-bis(diphenylphosphinoethane]dichloronickel (II) (0.350 gram, 0.663 mmol) in 45 milliliters of anhydrous THF in a 250 milliliter round-bottomed flask under an inert atmosphere, and refluxed for 24 hours. Thereafter, the reaction mixture was diluted with 200 milliliters of ethyl acetate, washed twice with water and then dried with anhydrous magnesium sulfate. A brown solid, obtained after evaporation of the solvent, was purified by column chromatography on silica gel and recrystallization yielding 1,4-bis(2-thienyl)-2,5-dioctyloxybenzene as a light yellow crystalline product in 45 percent yield.

The NMR spectrum of the above obtained compound was recorded at room temperature using a Bruker DPX 300 NMR spectrometer:

$^1$H NMR (CDCl$_3$): δ 7.52 (d, 2H), 7.35 (d, 2H), 7.26 (s, 2H) 7.12 (t, 2H), 1.58–1.20 (m, 20H), 1.90 (m, 4H), 0.92 (t, 6H).

b) Polymerization:

A solution of the above prepared 1,4-bis(2-thienyl)-2,5-dioctyloxybenzene (0.50 gram, 1.00 mmol) in 10 milliliters of chlorobenzene was added slowly to a well stirred mixture of FeCl$_3$ (0.400 gram, 2.466 mmol) in 5 milliliters of chlorobenzene in a 50 milliliter round-bottomed flask in a dry atmosphere. The resultant mixture was heated at 50° C. for 1 hour, then heated at 40° C. for 24 hours under a blanket of dry air. After the aforementioned heating polymerization, the mixture was diluted with 20 milliliters of dichloromethane and washed three times with water. The separated organic phase was stirred with 200 milliliters of 7.5 percent of aqueous ammonia solution for 30 minutes, then washed three times with water, and subsequently poured into methanol to precipitate the crude thienylene-arylene polymer product, which was purified by soxhlet extraction with methanol, hexane, and chlorobenzene. The molecular weights of the soluble fraction in THF were determined by the GPC technique to be M$_w$=4,600, M$_n$=4,200 relative to polystyrene standards.

Device Fabrication and Evaluation:

Thin film transistor devices were fabricated under ambient conditions using the above prepared thienylene-arylene semiconductor polymer (2) according to the general procedures illustrated herein. No precautions were taken to exclude ambient oxygen or light. Using the same dimension as the test device above for P3HT (W=5,000 μm and L=60 μm), the following average properties from at least five transistors were obtained for the polymer (2).

Mobility: ~5.5×10$^{-3}$ cm$^2$/V.sec
Initial on-off ratio: ~9.0×10$^5$
On-off ratio after 5 days: ~6.0×10$^5$
On-off ratio after 30 days: ~8.0×10$^4$ The large initial current on/off ratio (9×10$^5$) and the slow reduction in current on/off ratio over time of the TFT device with thienylene-arylene polymer (2) indicated that (2) possesses a much higher air stablity than P3HT against chemical doping by environmental oxygen.

Example II

Preparation of Thienylene-arylene (8)

a) 1,4-bis(5-bromo-2-thienyl)-2,5-dioctyloxybenzene

N-bromosuccinimide (1.031 grams, 5.794 mmol) was added to a well-stirred solution of 1,4-bis(2-thienyl)-2,5-dioctyloxybenzene (1.42 grams, 2.847 mmol) in a mixture of 25 milliliters of dichloromethane and 25 milliliters of acetic acid in a 250 milliliter round-bottomed flask. The reaction mixture was stirred overnight, 18 to 23 hours, and monitored by thin layer chromatography. The product was collected by filtration and washed with methanol, yielding 1.69 grams (90.4 percent) of 1,4-bis[2-(5-bromothienyl)]-2,5-dioctyloxybenzene as a white yellowish solid.

$^1$H NMR (CDCl$_3$): δ 7.20 (s, 2H), 7.08 (d, 2H), 4.10 (t, 4H), 1.90 (m, 4H), 1.60–1.20 (m, 20H), 0.92 (t, 6H).

b) 1,4-bis[5-(3-octyl-2-thienyl)-2-thienyl]-2,5-dioctyloxy benzene

A solution of 2-bromo-3-octylthiophene (1.800 grams, 6.533 mmol) in 7 milliliters of anhydrous THF was added slowly over a period of 20 minutes to a mechanically stirred suspension of magnesium turnings (0.238 grams, 9.79 mmol) in 3 milliliters of THF in a 250 milliliter round-bottomed flask under an inert argon atmosphere. The resultant mixture was stirred at 60° C. for 4 hours, and then cooled down to room temperature. The resultant mixture was then added via a cannula to a mixture of 1,4-bis(5-bromo-2-thienyl)-2,5-dioctyloxybenzene (1.650 grams, 2.513 mmol) and [1,3-bis(diphenylphosphinopropane] dichloronickel (II) (0.057 gram, 0.105 mmol) in 20 milliliters of anhydrous THF in a 250 milliliter round-bottomed flask under an inert atmosphere, and refluxed for 48 hours. Subsequently, the reaction mixture was diluted with 200 milliliters of ethyl acetate, was washed twice with water and dried with anhydrous magnesium sulfate. A brown solid, obtained after evaporation of the solvent, was purified by column chromotography on silica gel and recrystallized yielding 1,4-bis[5-(3-octyl-2-thienyl)-2-thienyl]-2,5-dioctyloxybenzene as a yellow crystalline product in 30 percent yield.

The NMR spectrum of the above obtained compound was recorded at room temperature using a Bruker DPX 300 NMR spectrometer:

$^1$H NMR (CDCl$_3$): δ 7.52 (d, 2H), 7.25 (s, 2H), 7.18 (d, 2H), 7.12 (d, 2H) 6.98 (d, 2H), 4.10 (t, 4H), 2.82 (t, 4H), 1.94 (m, 4H), 1.68 (m, 4H), 1.58–1.20 (m, 40H), 0.90 (m, 12H).

c) Polymerization

A solution of 1,4-bis[5-(3-octyl-2-thienyl)-2-thienyl]-2,5-dioctyloxybenzene (0.35 gram, 0.381 mmol) in 7 milliliters of chlorobenzene was added to a well stirred mixture of FeCl$_3$ (0.3 gram, 1.849 mmol) in 3 milliliters of chlorobenzene in a 50 milliliter round-bottomed flask in a dry atmosphere. The resultant mixture was stirred at 65° C. for 20 hours under a blanket of dry air. After the polymerization, the mixture was diluted with 20 milliliters of dichloromethane and washed with water three times. The separated organic phase was stirred with 100 milliliters of 7.5 percent of an aqueous ammonia solution for half an hour, washed with water again, and then poured into methanol to precipitate the crude thienylene-arylene polymer, which was purified by soxhlet extraction with methanol, heptane, and chlorobenzene. The molecular weights of the soluble fraction in THF were determined by the GPC technique to be $M_w$=9,600, $M_n$=6,300 relative to polystyrene standards.

Device Fabrication and Evaluation:

Thin film transistor devices were fabricated according to the general procedures illustrated herein under ambient conditions using the above prepared thienylene-arylene polymer. No precautions were taken to exclude ambient oxygen or light. Using the same dimension as P3HT (W=5,000 μm and L=60 μm), the following average properties from at least five transistors were obtained for the TFTs using the thienylene-arylene semiconductor polymer (8):

Mobility: 0.9 to 1.2×10$^{-2}$ cm$^2$/V.sec

Initial on-off ratio: ~1.5×10$^6$

On-off ratio after 5 days: ~9×10$^5$

On-off ratio after 30 days: ~2×10$^5$

The large initial current on/off ratio (1.5×10$^6$) and the slow reduction in current on/off ratio over time of the TFT device with thienylene-arylene polymer (8) evidences that (8) possesses a much higher air stablity than P3HT against chemical doping by environmental oxygen.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. An electronic device containing a thienylene-arylene polymer consisting of a repeating segment containing at two 2,5-thienylene units of (I) and one arylene unit of (IIIa)

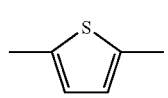

(I)

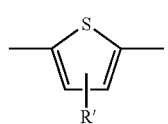

(II)

wherein each R is independently an alkoxy side chain; and a represents the number of R groups and a is 2.

2. A device in accordance with claim 1 wherein each R contains from about 1 to about 25 carbon atoms.

3. A device in accordance with claim 2 wherein a and b are 1 or 2.

4. A device in accordance with claim 1 wherein R is alkyl or alkoxy selected from the group consisting of pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, and pentadecyloxy.

5. A device in accordance with claim 1 wherein R' is alkyl or alkoxy selected from the group consisting of methyl, methoxy, ethyl, ethoxy, propyl, propoxy, butyl, butoxy, pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, and pentadecyloxy.

6. A device in accordance with claim 1 wherein said arylene is a dialkylphenylene or dialkoxyphenylene.

7. A device in accordance with claim 1 wherein arylene is dialkoxyphenylene.

8. A device in accordance with claim 1 wherein dialkoxyphenylene is selected from the group consisting of bis(pentyloxy)phenylene, bis(hexyloxy)phenylene, bis(heptyloxy)phenylene, bis(nonyloxy)phenylene, bis(undecyloxy)phenylene, bis(dodecyloxy) phenylene, bis(tridecyloxy) phenylene, bis(tetradecyloxy)phenylene, and bis(pentadecyloxy)phenylene.

9. A device in accordance with claim 7 wherein said dialkylphenylene is dioctylphenylene.

10. A device in accordance with claim 1 wherein said arylene is dialkylphenylene.

11. A device in accordance with claim 1 wherein said dialkylphenylene is selected from the group consisting of dipentylphenylene, dihexylphenylene, diheptylphenylene, dioctylphenylene, dinonylphenylene, didecylphenylene, bis(undecyl)phenylene, bis(dodecyl)phenylene, bis(tridecyl)phenylene, bis(tetradecyl)phenylene, and bis(pentadecyl)phenylene.

12. A device in accordance with claim 10 wherein said dialkylphenylene, or didecylphenylene.

13. A thin film transistor comprised of a substrate, a gate electrode, a gate dielectric layer, a source electrode and a drain electrode, and a semiconductor layer comprised of the thienylene-arylene polymer of claim 1.

14. A thin film transistor in accordance with claim 13 wherein R is alkoxy containing from about 5 to about 25 carbon atoms.

15. A thin film transistor in accordance with claim 13 wherein R' is halogen of a chlorine or bromine atom.

16. A thin film transistor in accordance with claim 13 wherein a and b are independently 1 or 2.

17. A thin film transistor in accordance with claim 13 wherein arylene is a dialkylphenylene or a dialkoxyphenylene.

18. A thin film transistor in accordance with claim 13 wherein said dialkoxyphenylene is selected from the group consisting of bis(pentyloxy)phenylene, bis(hexyloxy)phenylene, bis(heptyloxy)phenylene, bis(nonyloxy)phenylene, bis(undecyloxy)phenylene, bis(dodecyloxy) phenylene, bis(tridecyloxy)phenylene, bis(tetradecyloxy)phenylene, and bis(pentadecyloxy)phenylene.

19. A device in accordance with claim 17 wherein said dialkylphenylene is dioctylphenylene, didecylphenylene, bis(octyloxy)phenylene, or bis(decyloxy)phenylene.

20. A device in accordance with claim 1 wherein said arylene is a dialkoxyphenylene of bis(octyloxy)phenylene, or bis(decyloxy)phenylene.

21. A device in accordance with claim 1 wherein at least one is from 1 to about 50.

22. A device in accordance with claim 1 wherein at least one is from about 5 to about 100.

23. A device in accordance with claim 1 wherein at least one is 1.

24. A device in accordance with claim 1 wherein (IIIa) is selected.

25. A device in accordance with claim 1 wherein (IIIb) is selected.

26. A device in accordance with claim 1 wherein (IIIc) is selected.

27. A thin film transistor comprised of a substrate, a gate electrode, a gate dielectric layer, a source electrode, a drain electrode, and a semiconductor layer comprised of a polymer represented by Formula (IV-a) or (IV-b)

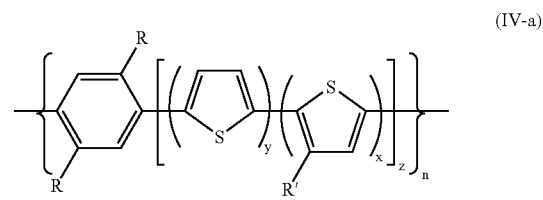

(IV-a)

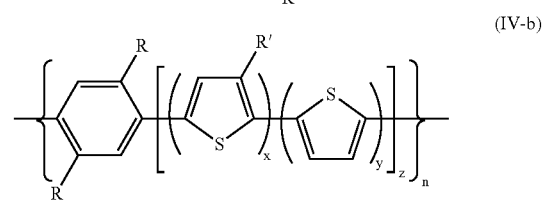

(IV-b)

wherein R is an alkyl or alkoxy of from about 5 to about 25 carbon atoms; R' is halogen, alkyl or alkoxy, each with about 1 to about 30 carbon atoms; x and y represent the number of units and are independently from 0 to about 10, provided that the sum of x and y is at least equal to 1; z is about 1 to about 5, and n is the degree of polymerization, or the number of repeating segments in said polymer, and wherein said n is optionally from about 5 to about 500.

28. A thin film transistor in accordance with claim 27 wherein R is pentyl, hexyl, heptyl, octyl, nonyl, decyl, undecyl, dodecyl, tridecyl, tetradecyl, pentyldecyl, pentyloxy, hexyloxy, heptyloxy, octyloxy, nonyloxy, decyloxy, undecyloxy, dodecyloxy, tridecyloxy, tetradecyloxy, or pentadecyloxy.

29. A thin film transistor in accordance with claim 27 wherein R' is methyl, ethyl, propyl, butyl, pentyl, hexyl, heptyl, octyl, nonyl, decyl, undecyl, dodecyl, tridecyl, tetradecyl, pentyldecyl, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, or pentadecyloxy.

30. A thin film transistor in accordance with claim 27 wherein x, y and z are each independently from about 1 to about 5.

31. A thin film transistor in accordance with claim 27 wherein said polymer is a thienylene-arylene semiconductor selected from (1) through (15)

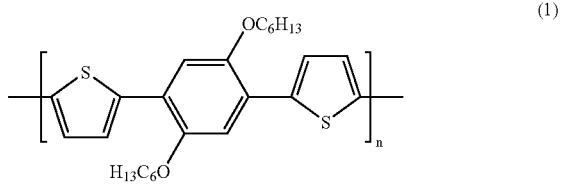

(1)

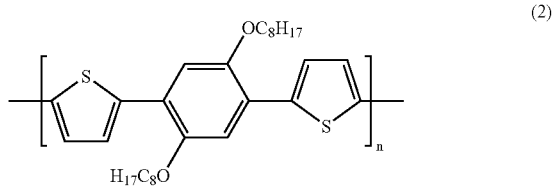

(2)

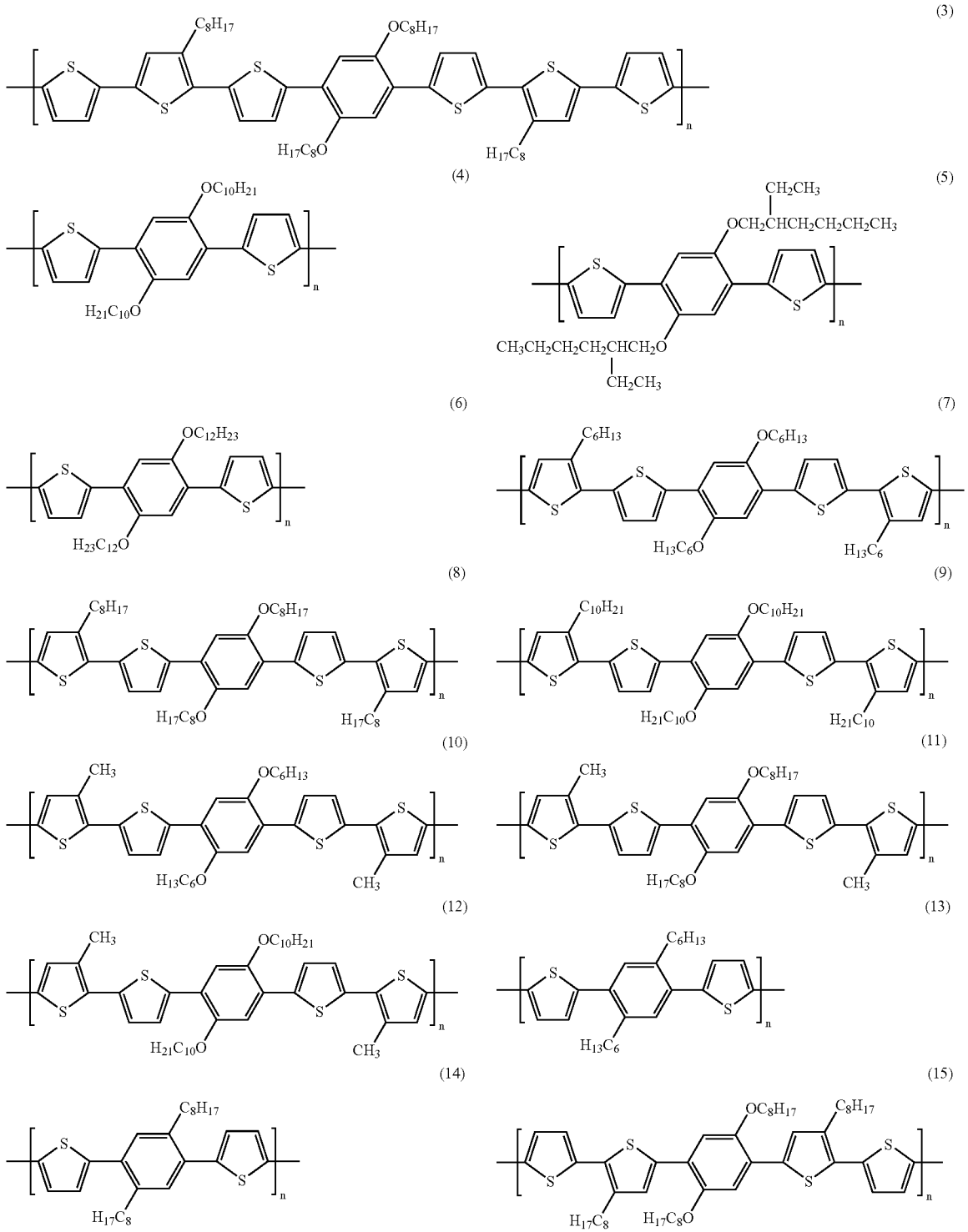

wherein n is from about 5 to about 200.

32. A thin film transistor in accordance with claim 27 wherein said substrate is a plastic sheet of a polyester, a polycarbonate, or a polyimide; said gate, source, and drain electrodes are each independently comprised of gold, nickel, aluminum, platinum, indium titanium oxide, a conductive polymer, a conductive ink or paste comprising a dispersion of conductive particles in a dispersing medium, and said gate dielectric layer is comprised of silicon nitride, silicon oxide, insulating polymers of a polyester, a polycarbonate, a polyacrylate, a poly(methacrylate), a poly(vinyl phenol), a polystyrene, a polyimide, an epoxy resin, an inorganic-organic composite material of nanosized metal oxide particles dispersed in a polymer, a polyimide, or an epoxy resin; and wherein said source/drain electrodes and said gate dielectric layer are in contact with said semiconductive layer.

33. A thin film transistor in accordance with claim 27 wherein said substrate is glass or a plastic sheet; said gate, source and drain electrodes are each independently comprised of gold; said gate dielectric layer is comprised of an organic polymer of poly(methacrylate), polyacrylate, poly(vinyl phenol), polystyrene, polyimide, polycarbonate, or a polyester, and wherein said source/drain electrodes and said gate dielectric layer are in contact with said semiconductive layer.

34. A thin film transistor in accordance with claim 27 wherein said polymer is a thienylene-arylene semiconductor layer formed by the solution process of spin coating, stamp printing, screen printing, or jet printing, and wherein said source/drain electrodes and said gate dielectric layer are in contact with said semiconductor layer.

35. A thin film transistor device in accordance with claim 27 wherein said gate, source and drain electrodes, dielectric, and semiconductor layers are formed from components deposited by solution processes of spin coating, solution casting, stamp printing, screen printing, and jet printing, and wherein said source/drain electrodes and said gate dielectric layer are in contact with said polymer layer.

36. A thin film transistor device in accordance with claim 27 wherein the substrate is a plastic sheet of a polyester or a polycarbonate, and the gate, source and drain electrodes are comprised of conductive polymers of polystyrene sulfonate-doped poly(3,4-ethylenedioxythiophene) or a conductive ink or paste of a colloidal dispersion of a metal of silver or gold in a binder, and the gate dielectric layer is an organic polymer or an inorganic oxide particle-polymer composite, and wherein said source/drain electrodes and said gate dielectric layer are in contact with said polymer layer.

37. A thin film transistor device in accordance with claim 27 wherein n is from about 50 to about 500, or from about 100 to about 350.

38. A thin film transistor in accordance with claim 27 wherein the number average molecular weight ($M_n$) of (IV-a) or (IV-b) is from about 2,000 to about 100,000, and the weight average molecular weight ($M_w$) thereof is from about 4,000 to about 300,000, each as measured by gel permeation chromatography using polystyrene standards.

39. A thin film transistor in accordance with claim 27 wherein the number average molecular weight ($M_n$) of (IV-a) or (IV-b) is from about 10,000 to about 50,000 and the weight average molecular weight ($M_w$) is from about 15,000 to about 100,000.

40. A thin film transistor in accordance with claim 27 wherein the thickness of the substrate is from about 500 micrometers to about 2 millimeters; the thickness of the gate dielectric layer is from about 100 nanometers to about 500 nanometers; the thickness of the polymer semiconductor layer is from about 50 nanometers to about 100 nanometers; and the thickness of the gate, source and drain electrode layer are each from about 50 nanometers to about 1 micrometer.

41. A device in accordance with claim 27 wherein (IV-a) is selected.

42. A device in accordance with claim 27 wherein (IV-b) is selected.

43. A thin film transistor comprised of a substrate, a gate electrode, a gate dielectric layer, a source electrode, a drain electrode, and a semiconductor layer comprised of a polymer selected from a thienylene-arylene semiconductor polymer (1) through (5)

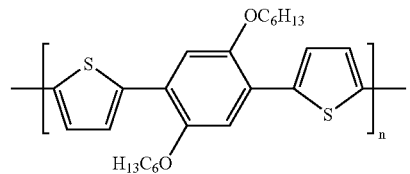

(1)

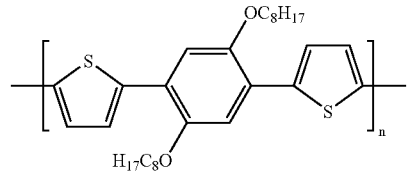

(2)

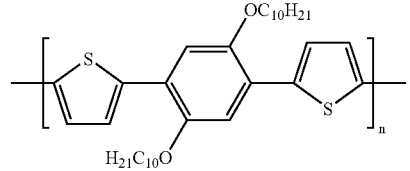

(3)

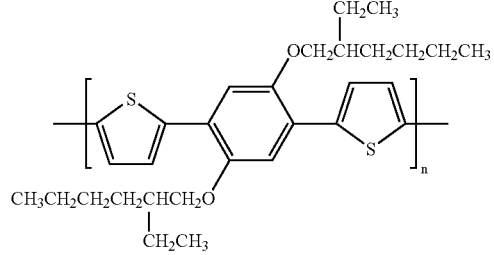

(4)

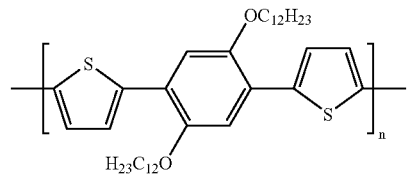

(5)

wherein n is from about 5 to about 500.

44. A thin film transistor in accordance with claim 43 wherein said polymer is a thienylene-arylene semiconductor polymer selected from the group consisting of semiconductor polymer (2), (4), (6), (7), (8), (9), (10), (11), (12), (17), (18), and (19), wherein n is from about 25 to about 160.

45. A thin film transistor comprised of a 2,5-thienylene repeating segment of (I) or (II), and at least one arylene segment of (IIIa), (IIIb), or (IIIc)

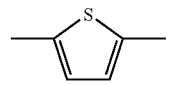

(I)

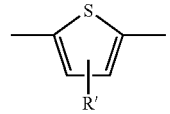

(II)

-continued (IIIa)

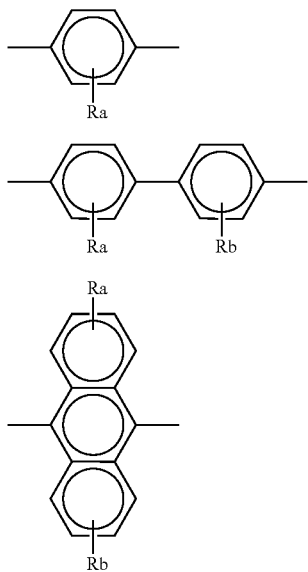

(IIIb)

(IIIc)

wherein each R is independently an alkyl or an alkoxy side chain; R' is halogen, alkyl, alkoxy, and a and b represent the number of R segments or groups.

46. An electronic device containing a thienylene-arylene polymer consisting of a repeating segment containing at least one 2,5-thienylene segment and at least one arylene segment, wherein the number of said arylene segments is from about 1 to about 3.

47. The electronic device of claim 46 wherein the 2,5-thienylene segment comprises at least one 2,5-thienylene unit of (I) or (II)

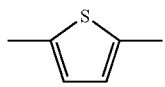 (I)

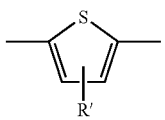 (II)

wherein R' is halogen, alkyl, or alkoxy.

48. The electronic device of claim 46 wherein the arylene segment comprises at least one arylene unit of (IIIa), (IIIb), or (IIIc)

(IIIa)

(IIIb)

(IIIc)

wherein each R is independently an alkyl or an alkoxy side chain; and a and b represent the number of R groups, and wherein the number of said arylene units (IIIa), (IIIb), and (IIIc) is from about 1 to about 3.

* * * * *

UNITED STATES PATENT AND TRADEMARK OFFICE
CERTIFICATE OF CORRECTION

PATENT NO. : 7,049,629 B2
APPLICATION NO. : 10/646389
DATED : May 23, 2006
INVENTOR(S) : Yiliang Wu et al.

It is certified that error appears in the above-identified patent and that said Letters Patent is hereby corrected as shown below:

The entire set of claims starting at Column 30, Line 29 and ending at Column 38, Line 43 should appear as follows:

1. An electronic device containing a thienylene-arylene polymer consisting of a repeating segment containing at least one 2,5-thienylene units of (I) and one arylene unit of (IIIa)

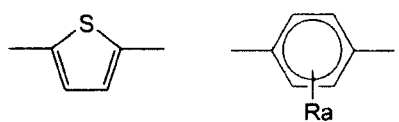

(I)          (IIIa)

wherein each R is independently an alkoxy side chain; and a represents the number of R groups and a is 2.

2. A device in accordance with claim 1 wherein each R contains from about 1 to about 25 carbon atoms.

3 A device in accordance with claim 1 wherein R is alkyl or alkoxy selected from the group consisting of pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, and pentadecyloxy.

Signed and Sealed this

Twenty-fifth Day of May, 2010

David J. Kappos
*Director of the United States Patent and Trademark Office*

4. A device in accordance with claim 7 wherein dialkoxyphenylene is selected from the group consisting of bis(pentyloxy)phenylene, bis(hexyloxy)phenylene, bis(heptyloxy)phenylene, bis(nonyloxy)phenylene, bis(undecyloxy)phenylene, bis(dodecyloxy) phenylene, bis(tridecyloxy)phenylene, bis(tetradecyloxy)phenylene, and bis(pentadecyloxy)phenylene.

5. A thin film transistor comprised of a substrate, a gate electrode, a gate dielectric layer, a source electrode and a drain electrode, and a semiconductor layer comprised of the thienylene-arylene polymer of claim 1.

6. A thin film transistor in accordance with claim 5 wherein R is alkoxy containing from about 5 to about 25 carbon atoms.

7. (Original) A thin film transistor in accordance with claim 5 wherein said dialkoxyphenylene is selected from the group consisting of bis(pentyloxy)phenylene, bis(hexyloxy)phenylene, bis(heptyloxy)phenylene, bis(nonyloxy)phenylene, bis(undecyloxy)phenylene, bis(dodecyloxy)phenylene, bis(tridecyloxy)phenylene, bis(tetradecyloxy)phenylene, and bis(pentadecyloxy)phenylene.

8. A thin film transistor comprised of a substrate, a gate electrode, a gate dielectric layer, a source electrode, a drain electrode, and a semiconductor layer comprised of a polymer selected from a thienylene-arylene semiconductor polymer (1) through (5)

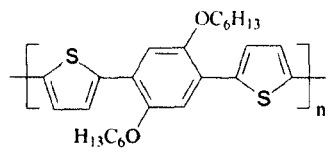

(1)

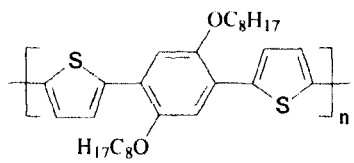
(2)
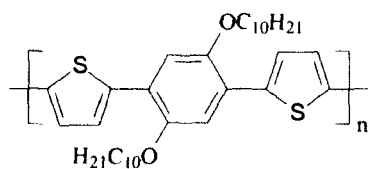
(3)
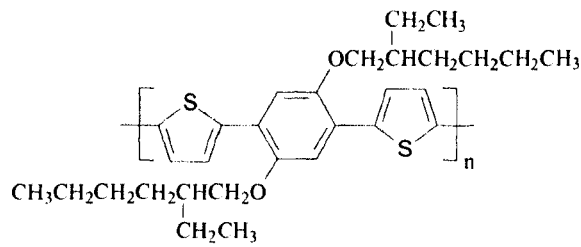
(4)
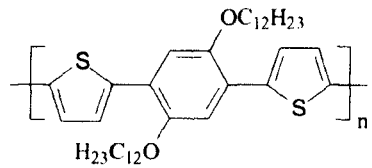
(5)
wherein n is from about 5 to about 500.
9. An electronic device containing a thienylene-arylene polymer consisting of a repeating segment containing at least one 2,5-thienylene segment and at least one arylene segment, wherein the number of said arylene segments is from about 1 to about 3.

10. The electronic device of claim 9 wherein the 2,5-thienylene segment comprises at least one 2,5-thienylene unit of (I) or (II)

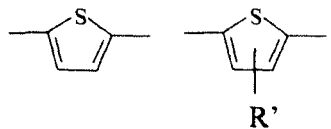

(I)　　(II)

wherein R' is halogen, alkyl, or alkoxy.

11. The electronic device of claim 9 wherein the arylene segment comprises at least one arylene unit of (IIIa), (IIIb), or (IIIc)

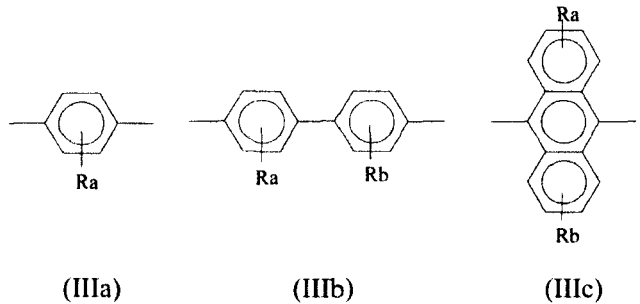

(IIIa)　　(IIIb)　　(IIIc)

wherein each R is independently an alkyl or an alkoxy side chain; and a and b represent the number of R groups, and wherein the number of said arylene units (IIIa), (IIIb), and (IIIc) is from about 1 to about 3.

12. A device in accordance with claim 2 wherein a and b are 1 or 2.

13. A device in accordance with claim 1 wherein R' is alkyl or alkoxy selected from the group consisting of methyl, methoxy, ethyl, ethoxy, propyl, propoxy, butyl, butoxy, pentyl, pentyloxy, hexyl, hexyloxy, heptyl, heptyloxy, octyl, octyloxy, nonyl, nonyloxy, decyl, decyloxy, undecyl, undecyloxy, dodecyl, dodecyloxy, tridecyl, tridecyloxy, tetradecyl, tetradecyloxy, pentadecyl, and pentadecyloxy.

14. A device in accordance with claim 1 wherein said arylene is a dialkylphenylene or dialkoxyphenylene.

15. A device in accordance with claim 1 wherein arylene is dialkoxyphenylene.

16. A device in accordance with claim 1 wherein said arylene is dialkylphenylene.

17. A device in accordance with claim 9 wherein said dialkylphenylene is selected from the group consisting of dipentylphenylene, dihexylphenylene, diheptylphenylene, dioctylphenylene, dinonylphenylene, didecylphenylene, bis(undecyl)phenylene, bis(dodecyl)phenylene, bis(tridecyl)phenylene, bis(tetradecyl)phenylene, and bis(pentadecyl) phenylene.

18. A thin film transistor in accordance with claim 5 wherein R' is halogen of a chlorine or bromine atom.

19. A thin film transistor in accordance with claim 5 wherein a and b are independently 1 or 2.

20. A thin film transistor in accordance with claim 5 wherein arylene is a dialkylphenylene or a dialkoxyphenylene.

21. A thin film transistor comprised of a substrate, a gate electrode, a gate dielectric layer, a source electrode, a drain electrode, and a semiconductor layer comprised of a polymer represented by Formula (IV-a) or (IV-b)

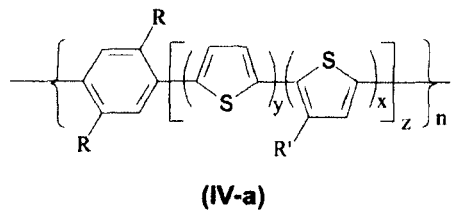

(IV-a)

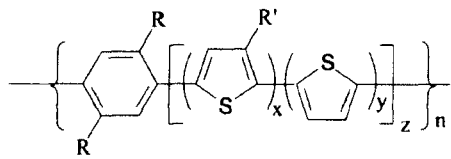

(IV-b)

wherein R is an alkyl or alkoxy of from about 5 to about 25 carbon atoms; R' is halogen, alkyl or alkoxy, each with about 1 to about 30 carbon atoms; x and y represent the number of segments and are optionally from 0 to about 10, provided that the sum of x and y is at least equal to 1; z is about 1 to about 5, and n is the degree of polymerization, or the number of repeating segments in said polymer, and wherein said n is optionally from about 5 to about 500.

22. A thin film transistor in accordance with claim 21 wherein R is pentyl, hexyl, heptyl, octyl, nonyl, decyl, undecyl, dodecyl, tridecyl, tetradecyl, pentyldecyl, pentyloxy, hexyloxy, heptyloxy, octyloxy, nonyloxy, decyloxy, undecyloxy, dodecyloxy, tridecyloxy, tetradecyloxy, or pentadecyloxy.

23. A thin film transistor in accordance with claim 21 wherein R' is methyl, ethyl, propyl, butyl, pentyl, hexyl, heptyl, octyl, nonyl, decyl, undecyl, dodecyl, tridecyl, tetradecyl, pentyldecyl, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, or pentadecyloxy.

24. A thin film transistor in accordance with claim 21 wherein x, y and z are each independently from about 1 to about 5.

25. A thin film transistor in accordance with claim 21 wherein said polymer is a thienylene-arylene semiconductor selected from (1) through (15)
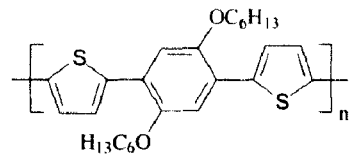
(1)
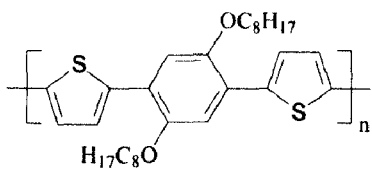
(2)
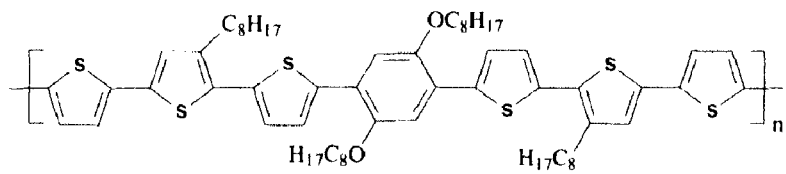
(3)
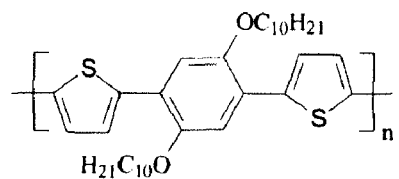
(4)

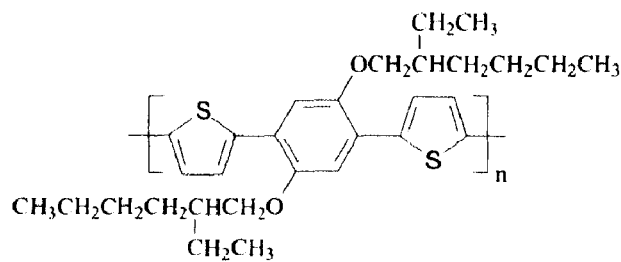
(5)
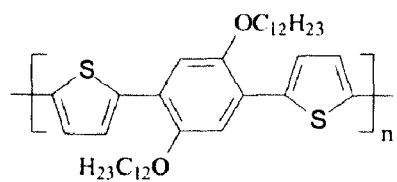
(6)
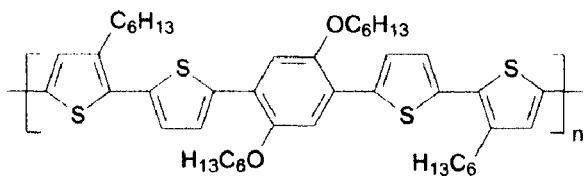
(7)
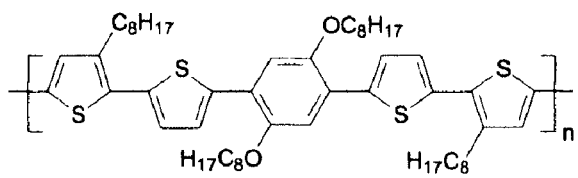
(8)

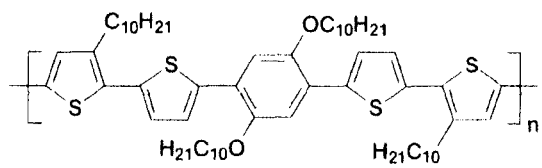
(9)
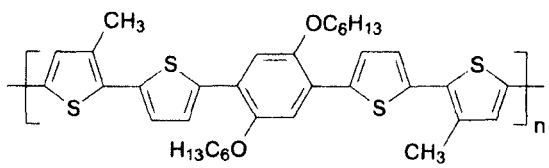
(10)
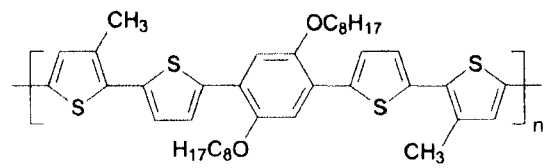
(11)
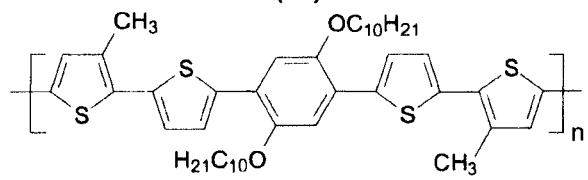
(12)
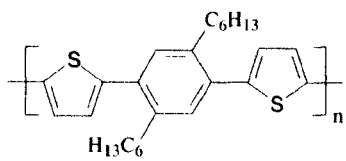
(13)
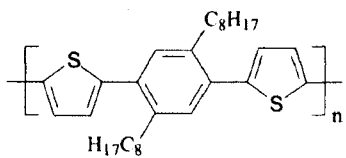
(14)

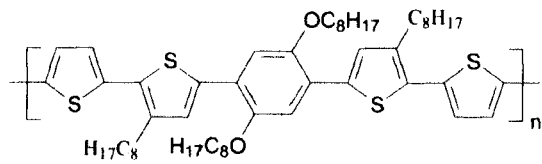

(15)

wherein n is from about 5 to about 200.

26. A thin film transistor in accordance with claim 8 wherein said polymer is a thienylene-arylene semiconductor polymer selected from the group consisting of semiconductor polymer (2), (4), (6), (7), (8), (9), (10), (11), (12), (17), (18), and (19) wherein n is from about 25 to about 160.

27. A thin film transistor in accordance with claim 21 wherein said substrate is a plastic sheet of a polyester, a polycarbonate, or a polyimide; said gate, source, and drain electrodes are each independently comprised of gold, nickel, aluminum, platinum, indium titanium oxide, a conductive polymer, a conductive ink or paste comprising a dispersion of conductive particles in a dispersing medium, and said gate dielectric layer is comprised of silicon nitride, silicon oxide, insulating polymers of a polyester, a polycarbonate, a polyacrylate, a poly(methacrylate), a poly(vinyl phenol), a polystyrene, a polyimide, an epoxy resin, an inorganic-organic composite material of nanosized metal oxide particles dispersed in a polymer, a polyimide, or an epoxy resin; and wherein said source/drain electrodes and said gate dielectric layer are in contact with said semiconductive layer.

28. A thin film transistor in accordance with claim 21 wherein said substrate is glass or a plastic sheet; said gate, source and drain electrodes are each independently comprised of gold; said gate dielectric layer is comprised of an organic polymer of poly(methacrylate), polyacrylate, poly(vinyl phenol), polystyrene, polyimide, polycarbonate, or a polyester, and wherein said source/drain electrodes and said gate dielectric layer are in contact with said semiconductive layer.

29. A thin film transistor in accordance with claim 21 wherein said polymer is a thienylene-arylene semiconductor layer formed by the solution process of spin coating, stamp printing, screen printing, or jet printing, and wherein said source/drain electrodes and said gate dielectric layer are in contact with said semiconductor layer.

30. A thin film transistor device in accordance with claim 21 wherein said gate, source and drain electrodes, dielectric, and semiconductor layers are formed from components deposited by solution processes of spin coating, solution casting, stamp printing, screen printing, and jet printing, and wherein said source/drain electrodes and said gate dielectric layer are in contact with said polymer layer.

31. A thin film transistor device in accordance with claim 21 wherein the substrate is a plastic sheet of a polyester or a polycarbonate, and the gate, source and drain electrodes are comprised of conductive polymers of polystyrene sulfonate-doped poly(3,4-ethylenedioxythiophene) or a conductive ink or paste of a colloidal dispersion of a metal of silver or gold in a binder, and the gate dielectric layer is an organic polymer or an inorganic oxide particle-polymer composite, and wherein said source/drain electrodes and said gate dielectric layer are in contact with said polymer layer.

32. A thin film transistor device in accordance with claim 21 wherein n is from about 50 to about 500, or from about 100 to about 350.

33. A thin film transistor in accordance with claim 21 wherein the number average molecular weight ($M_n$) of (IV-a) or (IV-b) is from about 2,000 to about 100,000, and the weight average molecular weight ($M_w$) thereof is from about 4,000 to about 300,000, each as measured by gel permeation chromatography using polystyrene standards.

34. A thin film transistor in accordance with claim 21 wherein the number average molecular weight ($M_n$) of (IV-a) or (IV-b) is from about 10,000 to about 50,000 and the weight average molecular weight ($M_w$) thereof is from about 15,000 to about 100,000.

35. A thin film transistor in accordance with claim 21 wherein the thickness of the substrate is from about 500 micrometers to about 2 millimeters; the thickness of the gate dielectric layer is from about 100 nanometers to about 500 nanometers; the thickness of the polymer semiconductor layer is from about 50 nanometers to about 100 nanometers; and the thickness of the gate, source and drain electrode layer are each from about 50 nanometers to about 1 micrometer.

36. A device in accordance with claim 1 wherein said arylene is a dialkoxyphenylene of bis(octyloxy)phenylene, or bis(decyloxy)phenylene.

37. A device in accordance with claim 16 wherein said dialkylphenylene, or didecylphenylene.

38. A device in accordance with claim 15 wherein said dialkylphenylene is dioctylphenylene.

39. A device in accordance with claim 20 wherein said dialkylphenylene is dioctylphenylene, didecylphenylene, bis(octyloxy)phenylene, or bis(decyloxy)phenylene.

40. A device in accordance with claim 1 wherein at least one is from 1 to about 50.

41. A device in accordance with claim 1 wherein at least one is from about 5 to about 100.

42. A device in accordance with claim 1 wherein at least one is 1.

43. A device in accordance with claim 1 wherein (IIIa) is selected.

44. A device in accordance with claim 1 wherein (IIIb) is selected.

45. A device in accordance with claim 1 wherein (IIIc) is selected.

46. A device in accordance with claim 21 wherein (IV-a) is selected.

47. A device in accordance with claim 21 wherein (IV-b) is selected.
48. A thin film transistor comprised of a 2,5-thienylene repeating segment of (I) or (II), and at least one arylene segment of (IIIa), (IIIb), or (IIIc)
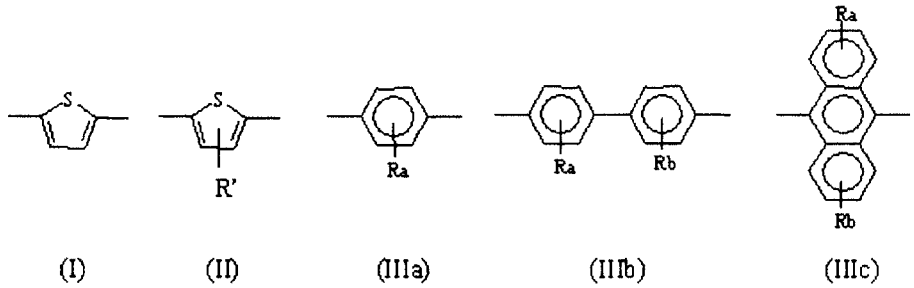
wherein each R is independently an alkyl or an alkoxy side chain; R' is halogen, alkyl, or alkoxy, and a and b represent the number of R segments or groups.

UNITED STATES PATENT AND TRADEMARK OFFICE
CERTIFICATE OF CORRECTION

| | | |
|---|---|---|
| PATENT NO. | : 7,049,629 B2 | Page 1 of 1 |
| APPLICATION NO. | : 10/646389 | |
| DATED | : May 23, 2006 | |
| INVENTOR(S) | : Yiliang Wu et al. | |

It is certified that error appears in the above-identified patent and that said Letters Patent is hereby corrected as shown below:

In the Specification

Column 1, lines 9 and 10, after "Cooperative Agreement No.", please delete "70NANBOH3033" and insert -- 70NANB0H3033 --.

Signed and Sealed this

Seventeenth Day of September, 2013

Teresa Stanek Rea
*Deputy Director of the United StatesPatent and Trademark Office*